United States Patent
Shiho

(10) Patent No.: US 10,290,365 B2
(45) Date of Patent: May 14, 2019

(54) IMAGE PROCESSING APPARATUS, IMAGE PROCESSING METHOD, AND NON-TRANSITORY COMPUTER READABLE MEDIUM

(71) Applicant: FUJI XEROX CO., LTD., Minato-ku, Tokyo (JP)

(72) Inventor: Yuichi Shiho, Kanagawa (JP)

(73) Assignee: FUJI XEROX CO., LTD., Minato-Ku, Tokyo (JP)

( * ) Notice: Subject to any disclaimer, the term of this patent is extended or adjusted under 35 U.S.C. 154(b) by 733 days.

(21) Appl. No.: 14/462,781

(22) Filed: Aug. 19, 2014

(65) Prior Publication Data

US 2015/0261919 A1 Sep. 17, 2015

(30) Foreign Application Priority Data

Mar. 17, 2014 (JP) ................. 2014-053605

(51) Int. Cl.
*G16H 10/60* (2018.01)
*G06K 9/00* (2006.01)
*G06F 19/00* (2018.01)

(52) U.S. Cl.
CPC ............ *G16H 10/60* (2018.01); *G06F 19/00* (2013.01); *G06F 19/321* (2013.01); *G06K 9/00483* (2013.01)

(58) Field of Classification Search
CPC .... H04N 1/00; G06T 1/00; G06K 1/00; G06F 3/00; G06F 9/00
See application file for complete search history.

(56) References Cited

U.S. PATENT DOCUMENTS 6,301,592 B1 * 10/2001 Aoyama .................. G06F 8/71
 715/229
7,587,431 B1 * 9/2009 Rao ...................... G06F 11/1471
(Continued)

FOREIGN PATENT DOCUMENTS

JP 09-098961 A 4/1997
JP 2001-125995 A 5/2001
(Continued)

OTHER PUBLICATIONS

Communication dated May 19, 2015 from the Japanese Patent Office in counterpart application No. 2014-053605.
(Continued)

*Primary Examiner* — Linh Giang Le
(74) *Attorney, Agent, or Firm* — Sughrue Mion, PLLC

(57) ABSTRACT

An image processing apparatus includes a difference image generator that receives a collection of medical record sheet image data that is generated by reading an image of a medical record sheet with content thereof updated in a time sequence, extracts a difference between preceding medical record sheet image data and current medical record sheet image data, and acquires a sequential collection of difference image data representing an updated written portion of the medical record sheet by extracting a difference in each image reading cycle, a memory processing unit that associates the difference image data with attribute information related to writing, and causes a memory to store the resulting difference image data, and an output processing unit that selects output image data from the collection of difference image data and outputs the selected output image data.

20 Claims, 16 Drawing Sheets

(56) References Cited

U.S. PATENT DOCUMENTS

| | | | |
|---|---|---|---|
| 8,176,004 B2* | 5/2012 | Malaney | G06Q 10/00 707/608 |
| 2009/0257653 A1* | 10/2009 | Ashikaga | G06K 9/00442 382/173 |
| 2014/0082469 A1* | 3/2014 | Sitrick | G06Q 10/10 715/205 |
| 2014/0195899 A1* | 7/2014 | Bastide | G06F 17/24 715/256 |

FOREIGN PATENT DOCUMENTS

| | | |
|---|---|---|
| JP | 2003-060894 A | 2/2003 |
| JP | 2006-343865 A | 12/2006 |
| JP | 2007-122210 A | 5/2007 |
| JP | 2009-182870 A | 8/2009 |
| JP | 2009-258815 A | 11/2009 |
| JP | 2011-125402 A | 6/2011 |
| JP | 2013-117908 A | 6/2013 |

OTHER PUBLICATIONS

Communication dated Oct. 26, 2017 from the State Intellectual Property Office of the P.R.C. in counterpart Application No. 201410505198.9.

* cited by examiner

NURSING RECORD SHEET

FIG. 7

| ID | PATIENT ID | DOCUMENT NO. | PAGE NO. - REGION NO. | DOCUMENT TYPE | TOP-LEFT COORDINATES OF IMAGE | BOTTOM-RIGHT COORDINATES OF IMAGE | RECORDER | DATE AND TIME OF EVENT | SCANNING OPERATOR | DATE AND TIME OF SCANNING |
|---|---|---|---|---|---|---|---|---|---|---|
| 00001 | P0123456 | 101 | 2 | 1 (CLINICAL CHART) | (100, 100) | (900, 200) | D0001 | 2013/11/01 09:00:00 | N0011 | 2013/11/01 16:00:00 |
| 00002 | P0123456 | 101 | 2 | 1 | (100, 300) | (500, 400) | D0002 | 2013/11/08 10:00:00 | N0011 | 2013/11/08 16:05:00 |
| 00003 | P0123456 | 102 | 1-1 | 2 (FEVER CHART) | (100, 100) | (900, 700) | N0011 | 2013/11/09 20:00:00 | N0011 | 2013/11/10 16:00:00 |
| 00004 | P0123456 | 102 | 1-3 | 3 (NURSING RECORD) | (100, 2000) | (1200, 2100) | N0011 | 2013/11/09 20:00:00 | N0011 | 2013/11/10 16:00:00 |
| 00005 | P0123456 | 103 | 1 | 21 (PHYSIOLOGICAL FUNCTION TEST REPORT) | — | — | E0022 | 2013/11/11 10:00:00 | N0031 | 2013/11/11 16:05:00 |

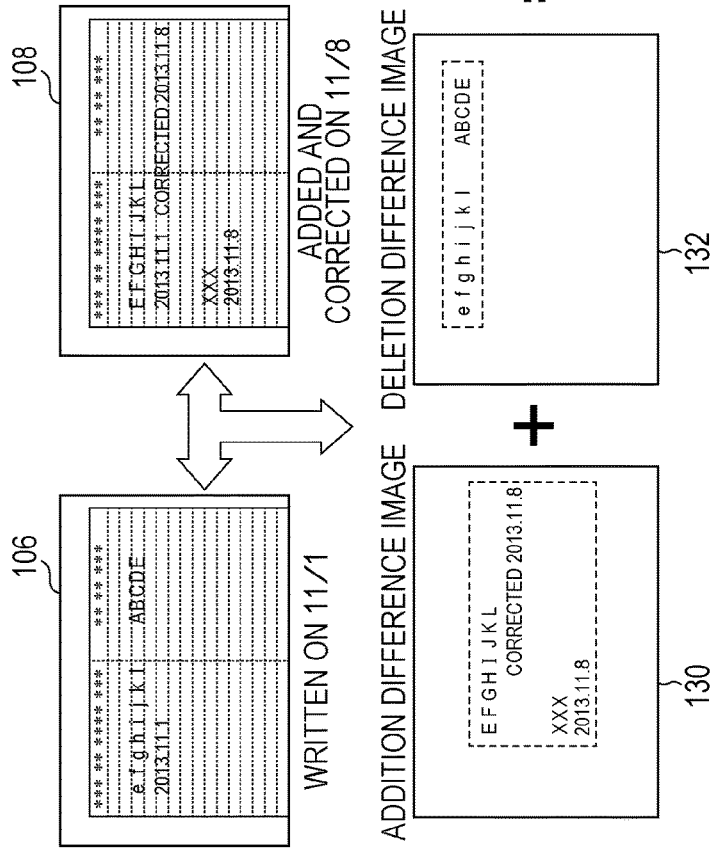
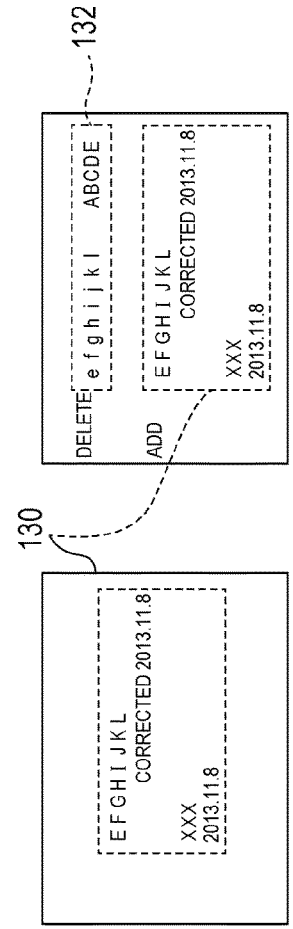
FIG. 12A
FIG. 12B

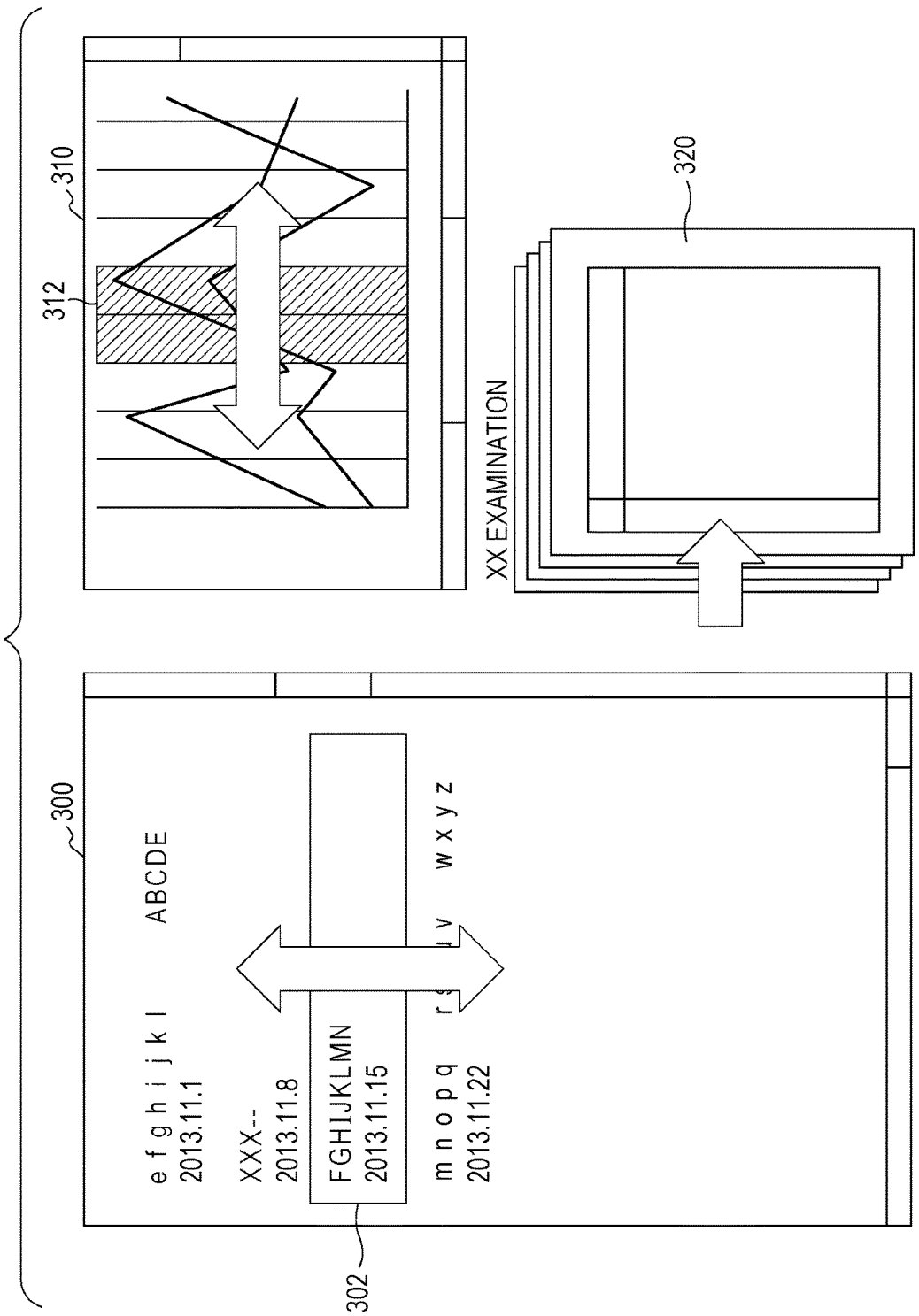

IMAGE PROCESSING APPARATUS, IMAGE PROCESSING METHOD, AND NON-TRANSITORY COMPUTER READABLE MEDIUM

CROSS-REFERENCE TO RELATED APPLICATIONS

This application is based on and claims priority under 35 USC 119 from Japanese Patent Application No. 2014-053605 filed Mar. 17, 2014.

BACKGROUND (i) Technical Field

The present invention relates to an image processing apparatus, an image processing method, and a non-transitory computer readable medium.

(ii) Related Art

There is a system that digitizes a paper document and allows a person to view a digital document on a personal computer or the like. For example, a paper document may be read using a reading device, such as a scanner, to generate digital image data. Digitizing the paper document in this way provides a system excellent in terms of information share, portability, and searchability, and useful in user applications.

SUMMARY

According to an aspect of the invention, an image processing apparatus is provided. The image processing apparatus includes a difference image generator that receives a collection of medical record sheet image data that is generated by reading an image of a medical record sheet with content thereof updated in a time sequence, extracts a difference between the medical record sheet image data that is generated in a preceding image reading cycle and the medical record sheet image data that is generated in a subsequent image reading cycle, and acquires a sequential collection of difference image data representing an updated written portion of the medical record sheet by extracting a difference in each image reading cycle, a memory processing unit that associates the difference image data with attribute information related to writing, and causes a memory to store the difference image data with the attribute information associated therewith, and an output processing unit that selects output image data from the collection of difference image data in accordance with a specified image selection condition and the attribute information and outputs the selected output image data.

BRIEF DESCRIPTION OF THE DRAWINGS

Exemplary embodiments of the present invention will be described in detail based on the following figures, wherein:

FIG. 7 illustrates a management table of image data;

FIGS. 12A and 12B diagrammatically illustrate a fourth display process operation;

FIG. 13 diagrammatically illustrates a fifth display process operation;

DETAILED DESCRIPTION

Figure 1:
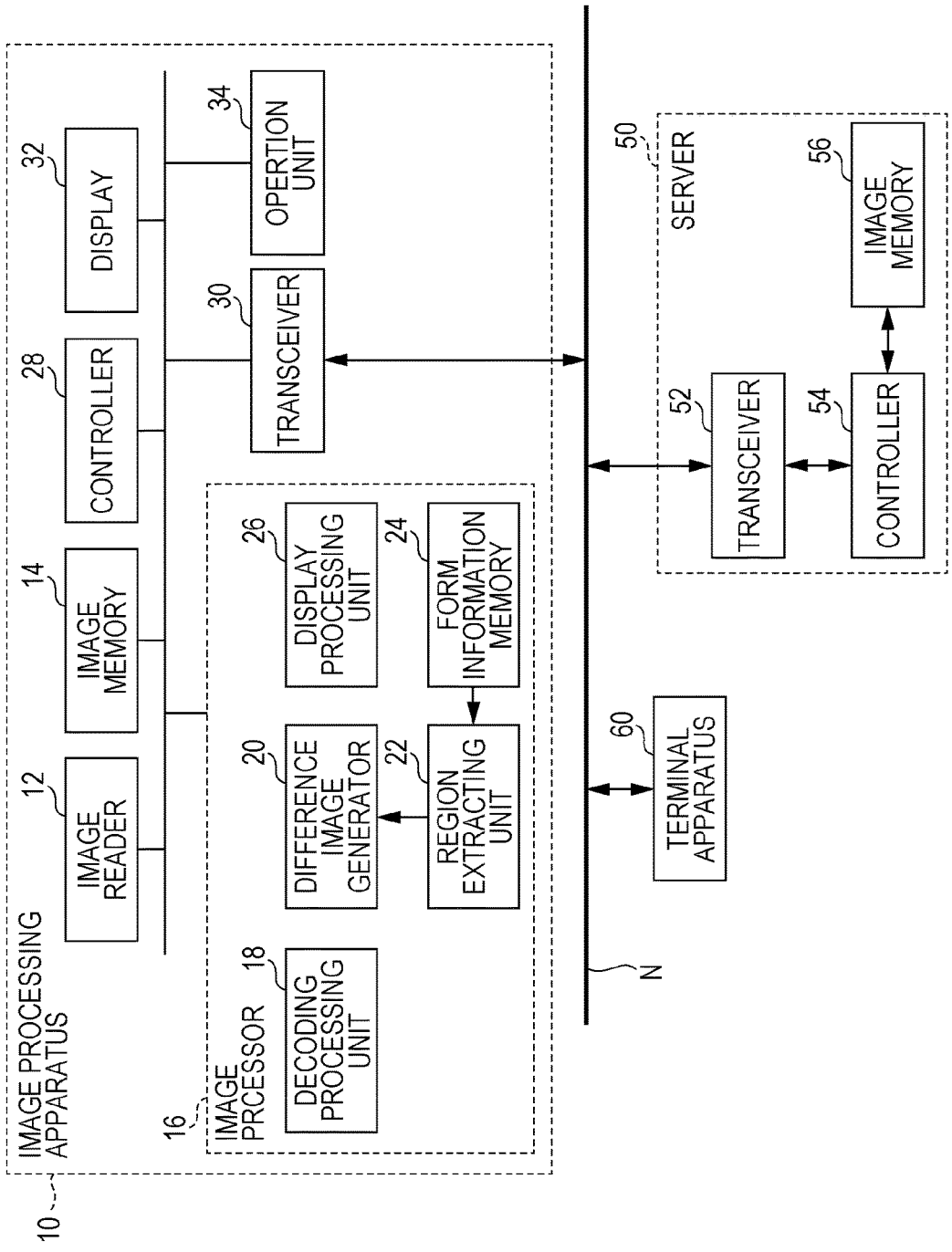
FIG. 1 is a block diagram illustrating an example of an image processing apparatus of an exemplary embodiment of the present invention.

FIG. 1 illustrates an image processing apparatus 10 of an exemplary embodiment of the present invention. The image processing apparatus 10 is connected to a server 50 through a communication network N. As described in detail below, the image processing apparatus 10 generates medical record sheet image data by reading an image on a medical record sheet and transmits the medical record sheet image data to the server 50 through the communication network N. A terminal apparatus 60 may be connected to the communication network N.

The medical record sheet is a sheet for use in a medical institution, such as a hospital. The medical record sheets include a clinical chart, an examination record sheet, a care record sheet, and a prescription.

Management information to manage the medical record image data may be pre-printed on the medical record sheet. The management information is encoded information (code information) of basic medical information. The basic medical information includes sheet type information indicating a type of medical record sheet (such as a paper clinical chart, an examination record sheet, or a nursing record sheet), a page number of the medical record sheets, the patient identification (ID) of a patient, patient name information indicating a patient name, medical service section information indicating a medical service, and event date and time information indicating the date and time of an event. For example, the event includes diagnosing, or writing to a medical record sheet. The event date and time information includes diagnosing date and time information indicating the date and time at which the patient is diagnosed, and writing date and time information indicating the date and time at which writing is performed on the medical record sheet. In the exemplary embodiment, the "writing" includes the action of "new writing" to the medical record sheet, addition (additional writing), and correction of the written content of the medical record sheet (including deletion of part or whole of the written content of the medical record sheet). The writing date and time thus indicates the date and time at which the writing is performed on the medical record sheet, the date and time at which addition is made, or the date and time at which a correction is made. The encoded information is generated by encoding the basic medical information in accordance with a predetermined encoding condition. For example, the encoded information is printed on the medical record sheet as a two-dimensional barcode into which the basic medical information is encoded. The image of the medical record sheet is read and medical record sheet image data is generated. The encoded information is decoded and the medical basic information (decoded information) is thus generated. The medical record sheet image data is managed in accordance with the decoded basic medical information. The elements of the image processing apparatus 10 are described below.

An image reader 12 is an image reading device, such as a scanner or a digital camera. The image reader 12 generates digital image data by reading the image on the medical record sheet. In the present embodiment, the image reader 12 repeatedly reads the image on the same medical record sheet having the content updated in a time sequence. In this way, multiple pieces of medical record sheet image data representing the medical record sheet are generated. For example, each time addition is made on the medical record sheet, the image reader 12 reads the image on the medical record sheet to generate the medical record sheet image data. Multiple pieces of medical record sheet image data are stored on an image memory 14.

An image processor 16 in the image processing apparatus 10 includes a decoding processing unit 18, a difference image generator 20, a region extracting unit 22, a form information memory 24, and a display processing unit 26.

If the encoded information such as the two-dimensional barcode is printed on the medical record sheet, the decoding processing unit 18 decodes the encoded information represented in the medical record sheet image data in accordance with a predetermined decoding condition. The basic medical information is thus obtained. The decoding processing unit 18 attaches (associates) the decoded basic medical information as attribute information to (with) the medical record sheet image data, and then causes the image memory 14 to store the medical record sheet image data with the basic medical information associated therewith.

If the encoded information is not printed on the medical record sheet, an operator simply input the basic medical information using an operation unit 34. In such a case, the basic medical information input by the operator is attached to the medical record sheet image data.

If new medical record sheet image data is generated by the image reader 12, the difference image generator 20 retrieves from the image memory 14 the medical record sheet image data generated in a preceding reading cycle (preceding image data) and the medical record sheet image data generated in a current reading cycle (current image data), and extracts a difference between the preceding image data and the current image data. Difference image data is thus generated. For example, the difference image generator 20 generates addition difference data representing a newly added portion to the medical record sheet. More specifically, the difference image generator 20 generates the addition difference image data representing a portion (addition region) that is included in the current image data but not included in the preceding image data. The difference image generator 20 may generate deletion difference image data representing a newly deleted portion from the medical record sheet. More specifically, the difference image generator 20 generates the deletion difference image data representing a portion (deletion region) that is not included in the current image data but included in the preceding image data.

The difference image generator 20 attaches to (associates with) difference image data, difference region location information representing the location of a difference region (addition region and deletion region) in the medical record sheet, and the decoded basic medical information, as the attribute information, and causes the image memory 14 to store the difference image data with the attribute information attached thereto. The difference image generator 20 may also include, in the attribute information, operator identification information (such as operator ID) identifying an operator of the image reading, and scanning date and time information indicating the date and time at which the scanning operation is performed, and may attach the attribute information to the difference image data. The operator may enter the operator identification information and the scanning date and time information using the operation unit 34. If the operator logs in on the image processing apparatus 10 with the operator identification information entered, the difference image generator 20 may attach the operator identification information input at the login to the difference image data as the attribute information. The difference image generator 20 may attach information indicating the date and time at the login to the difference image data as the scanning date and time information. Using the operation unit 34, the operator may enter writing date and time information indicating the date and time at which the writing is performed on the medical record sheet. In this case, the difference image generator 20 may include, in the attribute information, the entered writing date and time information, and attach the attribute information to the difference image data.

The region extracting unit 22 identifies a document type of each region in the medical record sheet represented in the medical record sheet image data, based on predetermined sheet form information. The region extracting unit 22 extracts region image data representing each region from the medical record sheet image data. For example, the document type includes a hand-written medical record (a written portion of a clinical chart, a written portion of a nursing record, a prescription or the like), examination data (such as blood test data), medical images (X-ray photograph, or computer tomography (CT) image). For example, the medical record sheet includes a medical record column (memo column) where a medical record is hand-written, an examination data column where examination data is written or a examination data sheet is glued, and a medical image column where a medical image, such as a photograph is glued. The sheet form information is location information indicating the location of the medical record column in the medical record sheet, the location of the examination data column, and the location of the medical image column. Based on the sheet form information, the region extracting unit 22 identifies the location of the medical record column, the location of the examination data column, and the location of the medical image in the medical record sheet image data, and separates, from the medical record sheet image data, the region image data of the medical record column, the region image data of the examination data column, and the region image data of the medical image column. The region extracting unit 22 thus extracts the region image data of each column from the medical record sheet image data. The region extracting unit 22 attaches the attribute information attached to the original medical record sheet image data to the region image data. The region extracting unit 22 further attaches, to the region image data, the document type information indicating the document type of the region image data, and the region location information indicating the location of the region in the medical record sheet, as the attribute information. The region image data is stored on the image memory 14.

When the region image data is extracted by the region extracting unit 22, the difference image generator 20 performs a difference process operation responsive to the document type of each region. For example, the difference image generator 20 does not extract a difference between the preceding image data and the current image data in the examination data and the medical image, but extracts a difference in the medical record columns (the written content of the clinical chart, the written content of the nursing record, or the prescription). More specifically, the difference image generator 20 extracts a difference in the medical record column between the preceding region image data and the current region image data. The difference image data representing the difference in the medical record column is thus generated. The difference image generator 20 attaches, to the difference image data, difference location information representing the location of the difference in the medical record sheet and the attribute information attached to the region image data. The difference image data is stored on the image memory 14. In the exemplary embodiment, the difference image generator 20 extracts the difference in a text portion (a medical record portion) in the medical record sheet.

The form information memory 24 pre-stores the sheet form information. The sheet form information is prepared for each type of the medical record sheet. More specifically, the prepared sheet form information includes sheet form information for a clinical chart, sheet form information for a nursing record sheet, and sheet form information for an examination record sheet. These pieces of sheet form information are stored on the form information memory 24. Sheet type information indicating the type of the medical record sheet is associated with the sheet form information. Based on the sheet form information responsive to the type of the medical record sheet, the region extracting unit 22 extracts the region image data of each region from the medical record sheet image data. The region extracting unit 22 may also identify the sheet form information based on the sheet type information included in the decoded basic medical information. If the operator enters the sheet type information using the operation unit 34, the region extracting unit 22 may identify the sheet form information based on the sheet type information entered by the operator.

The region extracting unit 22 and the form information memory 24 may not necessarily have to be included in the image processing apparatus 10. In such a case, the region image data is not generated in the image processing apparatus 10.

The display processing unit 26 retrieves image data (corresponding to output image data) from the image memory 14 in accordance with an image selection condition specified by the user, and performs a display process operation based on the retrieved image data. For example, if the user specifies the writing date and time on the medical record sheet, the display processing unit 26 retrieves the difference image data associated with the writing date and time information indicating the writing date and time, and performs the display process operation. The difference image data retrieved by the display processing unit 26 is output to the display 32 to be displayed there.

The controller 28 controls the elements of the image processing apparatus 10 in operation. In the exemplary embodiment, the controller 28 operates on the medical record sheet image data in one of a registration mode, a difference process mode, and a display process mode. When the difference image data is processed in the registration mode, or the display process mode, the function of each element of the image processor 16 is performed.

The transceiver 30 is a network interface, and transmits and receives data through the communication network N. In the exemplary embodiment, the transceiver 30 may transmit, to the server 50, the medical record sheet image data, the difference image data, and the region image data. The server 50 then stores the medical record sheet image data, the difference image data, and the region image data in a predetermined storage area thereof.

The operation unit 34 includes a keyboard, a touchpanel, and the like. For example, the user may enter the basic medical information, the writing date and time information, the operator identification information, the scanning date and time information, the sheet type information, and the like using the operation unit 34.

The server 50 includes a transceiver 52, a controller 54, and an image memory 56. The transceiver 52 is a network interface, and receives the medical record sheet image data, the difference image data, and the region image data through the communication network N from the image processing apparatus 10. The controller 54 causes the image memory 56 to store the medical record sheet image data, the difference image data, and the region image data. In this way, the medical record sheet image data, the difference image data, and the region image data are stored on the server 50. In the exemplary embodiment, the medical record sheet image data, the difference image data, and the region image data are managed in accordance with the attribute information respectively attached thereto. For example, in the server 50, a folder is created for each patient based on the patient ID, and the medical record sheet image data, the difference image data, and the region image data are stored on the folder. A folder may also be created on an event date and time basis (diagnosis day or writing day) or on a per medical service section, and then the medical record sheet image data, the difference image data, and the region image data are stored on the created folder.

The terminal apparatus 60 retrieves the medical record sheet image data, the difference image data, and the region image data from the image processing apparatus 10 and the server 50 through the communication network N, and then displays these pieces of data thereon.

The image processing apparatus 10 may be implemented by a hardware resource operating in cooperation with software. More specifically, the image processing apparatus 10 includes a processor, such as a central processing unit (CPU) (not illustrated). The processor reads a program stored on a storage device (not illustrated), and executes the program. The function of the image processor 16 and the controller 28 is thus implemented. The program is stored on the storage device through a storage medium, such as a compact disk (CD) or a digital versatile disk (DVD), or a communication network.

Figure 2:
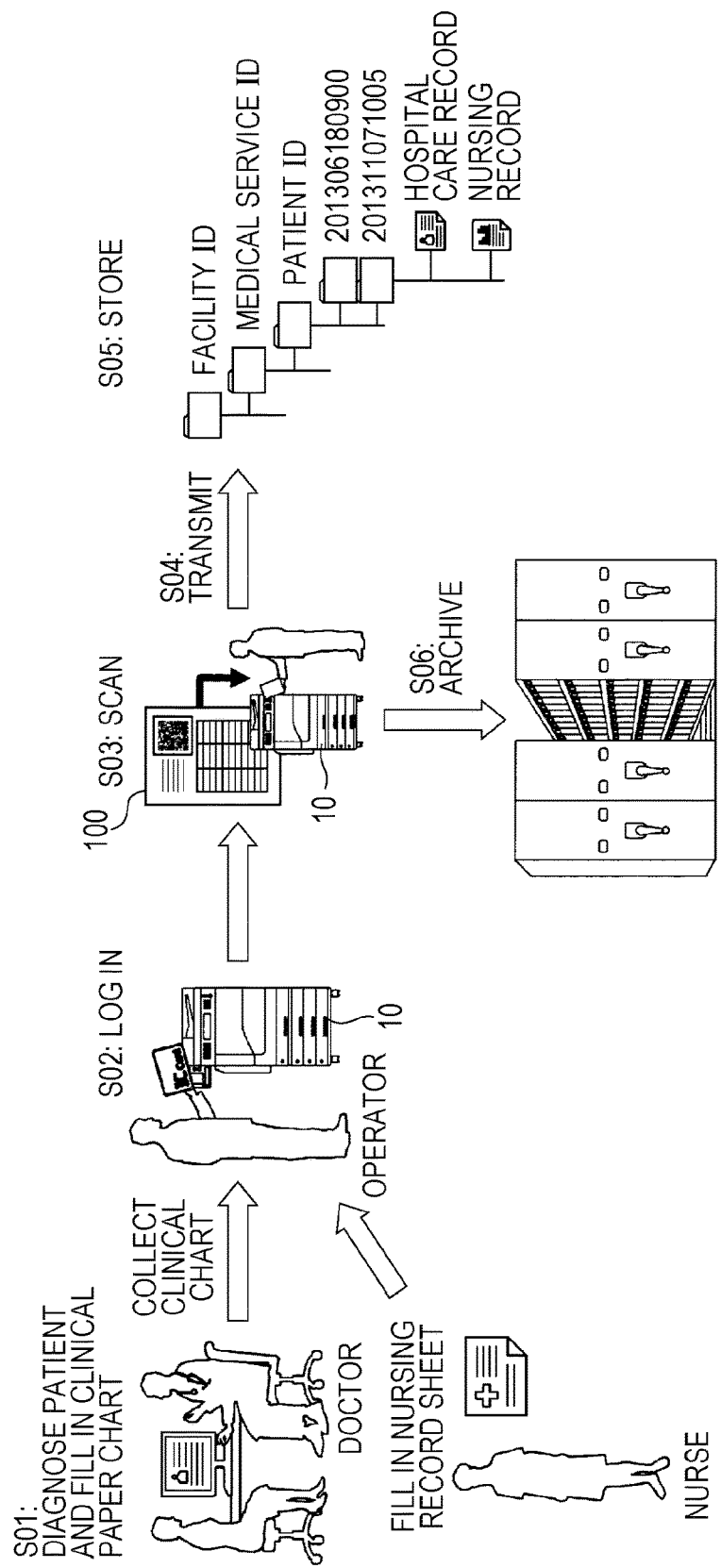
FIG. 2 illustrates the usage of medical record sheet image data.

A process performed on the medical record sheet image data during the registration mode is described below with reference to FIG. 2. In one operation example of the process, the medical record sheet image data is registered on the server 50. First, a doctor diagnoses a patient and writes diagnosis results of the patient on a paper clinical chart (S01). There are times when a nurse writes a nursing record on a nursing record sheet (S01). The operator logs in on the image processing apparatus 10 (S02). In response to an instruction from the operator, the image processing apparatus 10 reads images on the medical record sheet (such as the paper clinical chart or a nursing record sheet) (S03). The medical record sheet image data is thus generated. The basic medical information is attached to the medical record sheet image data by decoding the encoded information, such as a two-dimensional barcode. When the operator enters the basic medical information to the image processing apparatus 10, the entered basic medical information is attached to the medical record sheet image data. The medical record sheet image data is then transmitted from the image processing apparatus 10 to the server 50 (S04), and is then stored on the image memory 56 in the server 50 (S05). The server 50 then creates a folder on a per medical service section basis, on a per patient basis, or on a per event basis, and the medical record sheet image data is stored on the folder. The medical record sheet as the original is archived in a storage cabinet (S06).

Figure 3:
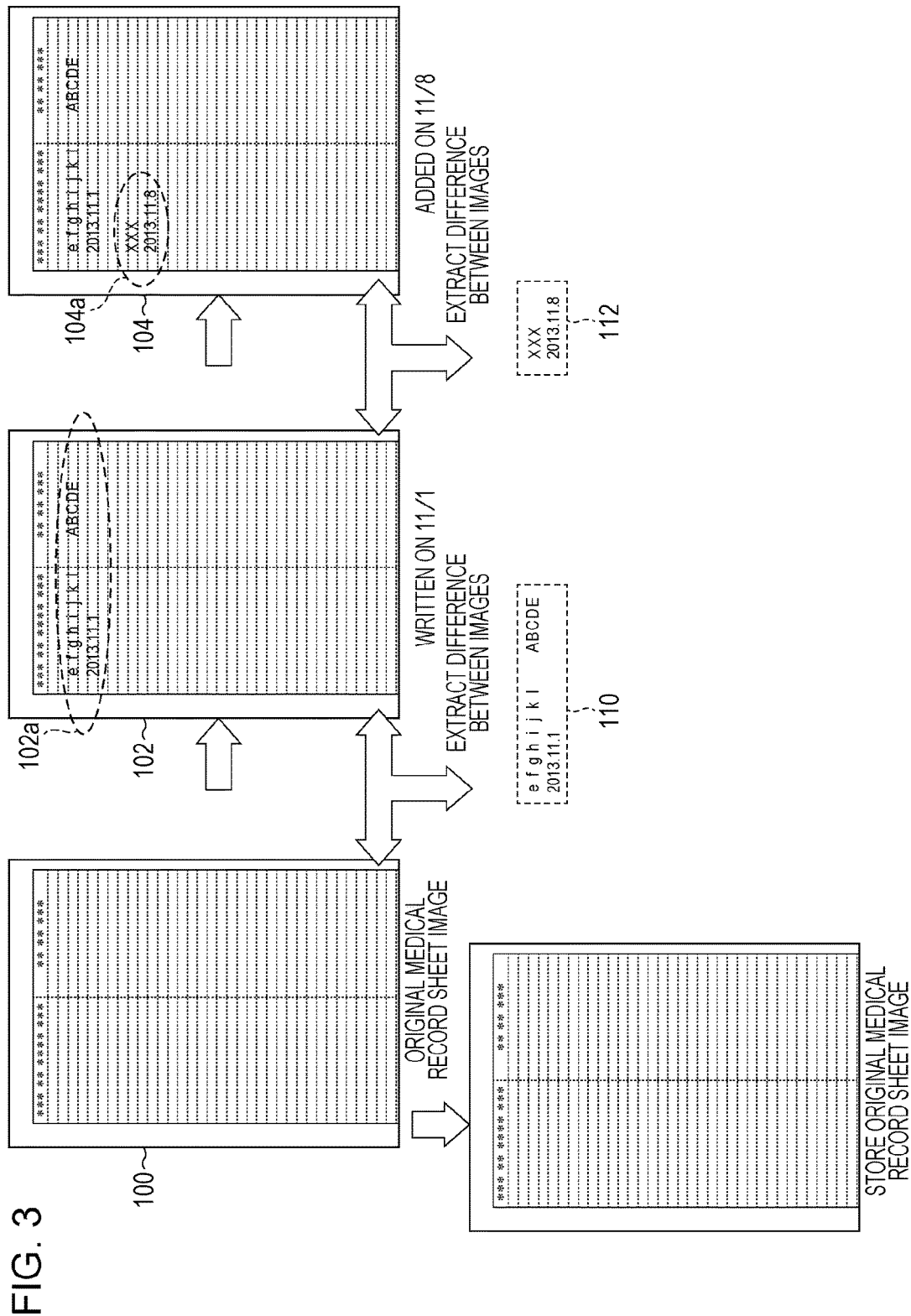
FIG. 3 diagrammatically illustrates a first difference process operation.

An operation in the difference process mode (a first difference process operation) is described with reference to FIG. 3. The image reader 12 reads an image on a blank medical record sheet (such as a blank paper clinical chart), and medical record sheet image data 100 representing the blank medical record sheet is generated. The basic medical information decoded by the decoding processing unit 18 or the basic medical information input by the operator using the operation unit 34 are attached to the medical record sheet image data 100.

In one operation example, writing may be performed on the medical record sheet, and the image on the filled medical record sheet may be read by the image reader 12 in November 1. The filled medical record sheet image data 102 is thus generated. The medical record sheet image data 102 represents an entry portion 102*a*. The basic medical information is attached to the medical record sheet image data 102. The difference image generator 20 extracts a difference between the medical record sheet image data 100 (preceding image data) generated in a preceding reading cycle and the medical record sheet image data 102 generated in a current reading cycle (current image data). Difference image data 110 representing the entry portion 102*a* corresponding to the difference is thus generated. The difference image data 110 corresponds to the addition difference image data. The difference image generator 20 generates the difference image data 110 representing a region including the entry portion 102*a* (a rectangular region that is identified by determining a circumscribing rectangle of a resulting difference image). The attribute information is attached to the difference image data 110. The attached attribute information include the difference region location information indicating the location of a difference region in the medical record sheet (the entry portion 102*a*), the writing date and time information indicating the date and time at which the entry portion 102*a* is written, the scanning date and time information, and the decoded basic medical information.

Addition may be made on the same medical record sheet, and the image on the medical record sheet subsequent to the addition may be read by the image reader 12 in November 8. The addition medical record sheet image data 104 is thus generated. The medical record sheet image data 104 includes an addition portion 104*a*. The basic medical information is attached to the medical record sheet image data 104 as well. The difference image generator 20 extracts a difference between the medical record sheet image data 102 generated in a preceding reading cycle (preceding image data) and the medical record sheet image data 104 generated in a current reading cycle (current image data). Difference image data 112 representing the addition portion 104*a* corresponding to the difference is thus generated. The difference image data 112 corresponds to the addition difference data. The attribute information is attached to the difference image data 112. The attached attribute information includes difference region location information indicating the location of a difference region in the medical record sheet (the addition portion 104*a*), the writing date and time information indicating the date and time at which the addition portion 104*a* is written, the scanning date and time information, and the decoded basic medical information.

The preceding image data may be reconstructed using the blank medical record sheet image data 100 and the difference image data. In such a case, a difference between the reconstructed preceding image data and the current image is extracted. For example, the difference image generator 20 may reconstruct the medical record sheet image data 102 (preceding image data) based on the blank medical record sheet image data 100 and the difference image data 110, and extracts a difference between the medical record sheet image data 102 (the preceding image data) and the medical record sheet image data (the current image data).

The difference image data 110 and 112 thus generated are stored on the image memory 14. The medical record sheet image data 100 through 104 may also be stored on the image memory 14. Each piece of image data stored in the image memory 14 is managed in accordance with the attribute information attached thereto. The difference image data 110 and 112 may be transmitted from the image processing apparatus 10 to the server 50 and stored on the image memory 56 in the server 50. The server 50 manages each piece of image data in accordance with the attribute information attached thereto. The medical record sheet image data 100 through 104 may be transmitted from the image processing apparatus 10 to the server 50 and stored on the server 50.

In the first difference process operation, the difference image data representing the portion added to the medical record sheet is generated. Since the addition is made on the medical record sheet in a time sequence (chronologically), multiple pieces of difference image data are generated in the time sequence. The addition portion is displayed by displaying the difference image data. For example, the multiple pieces of difference image data are arranged in the time sequence, and thus multiple addition portions are displayed in the time sequence.

Figure 4:
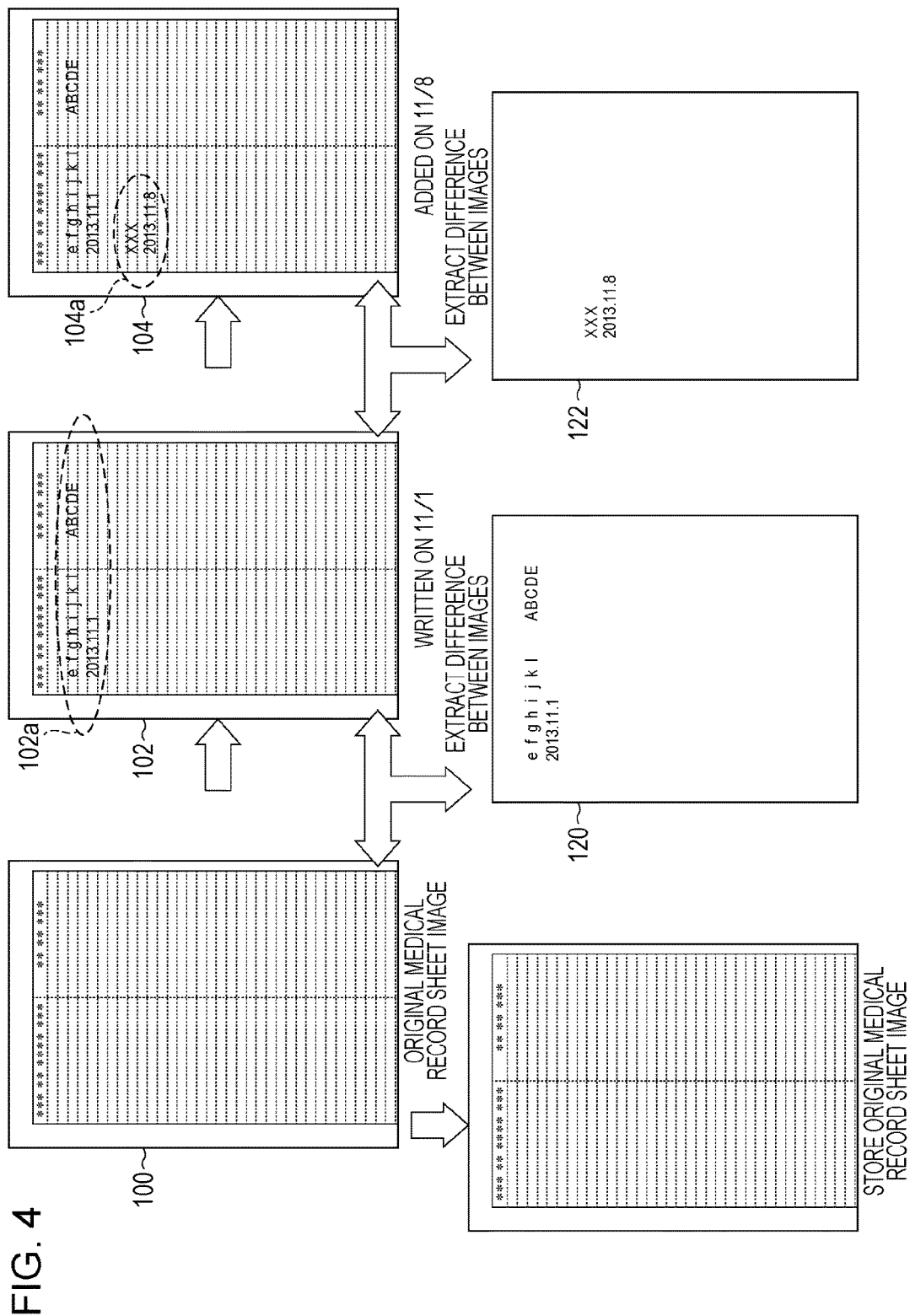
FIG. 4 diagrammatically illustrates a second difference process operation.

An operation in the difference process mode (a second difference process operation) is described with reference to FIG. 4. In the same manner as in the first difference process operation of FIG. 3, the image reader 12 reads the image on the blank medical record sheet to generate the blank medical record sheet image data 100.

Writing may be performed on the same medical record sheet, and the image on the medical record sheet subsequent to the writing may be read by the image reader 12 in November 1. The medical record sheet image data 102 subsequent to the writing is thus generated. The difference image generator 20 extracts a difference between the medical record sheet image data 100 (the preceding image data) generated in the preceding reading cycle and the medical record sheet image data 102 (the current image data) generated in the current reading cycle. The difference image generator 20 generates difference image data 120 of one page representing only the entry portion 102*a* corresponding to the difference. The difference image data 120 corresponds to the addition difference image data. The attribute information is attached to the difference image data 120. The attached attribute information includes a page number of the medical record sheet, the writing date and time information indicating the date and time at which the entry portion 102a is written, the scanning date and time information, and the decoded basic medical information.

Addition may be made on the same medical record sheet, and the image on the medical record sheet subsequent to the addition may be read by the image reader 12 in November 8. The addition medical record sheet image data 104 is thus generated. The difference image generator 20 extracts a difference between the medical record sheet image data 102 generated in the preceding reading cycle (the preceding image data) and the medical record sheet image data 104 generated in the current reading cycle (the current image data). The difference image generator 20 generates difference image data 122 of one page representing only the addition portion 104a corresponding to the difference. The difference image data 122 corresponds to the addition difference image data. The attribute information is attached to the difference image data 122. The attached attribute information includes a page number of the medical record sheet, the writing date and time information of the date and time at which the addition portion 104a is added, the scanning date and time information, and the decoded basic medical information.

In this way, the difference image data 120 and 122 is stored on the image memory 14. The difference image data 120 and 122 may be transmitted from the image processing apparatus 10 to the server 50 and stored on the image memory 56 in the server 50. The image memory 14 and the server 50 manage each piece of image data in accordance with the attribute information attached thereto. The medical record sheet image data 100 through 104 may be stored on the image memory 14 and the server 50.

The difference image data of one page representing an addition portion to the medical record sheet is generated in the second difference process operation. In the same manner as in the first difference process operation, multiple pieces of difference image data are generated in the time sequence.

Figure 5:
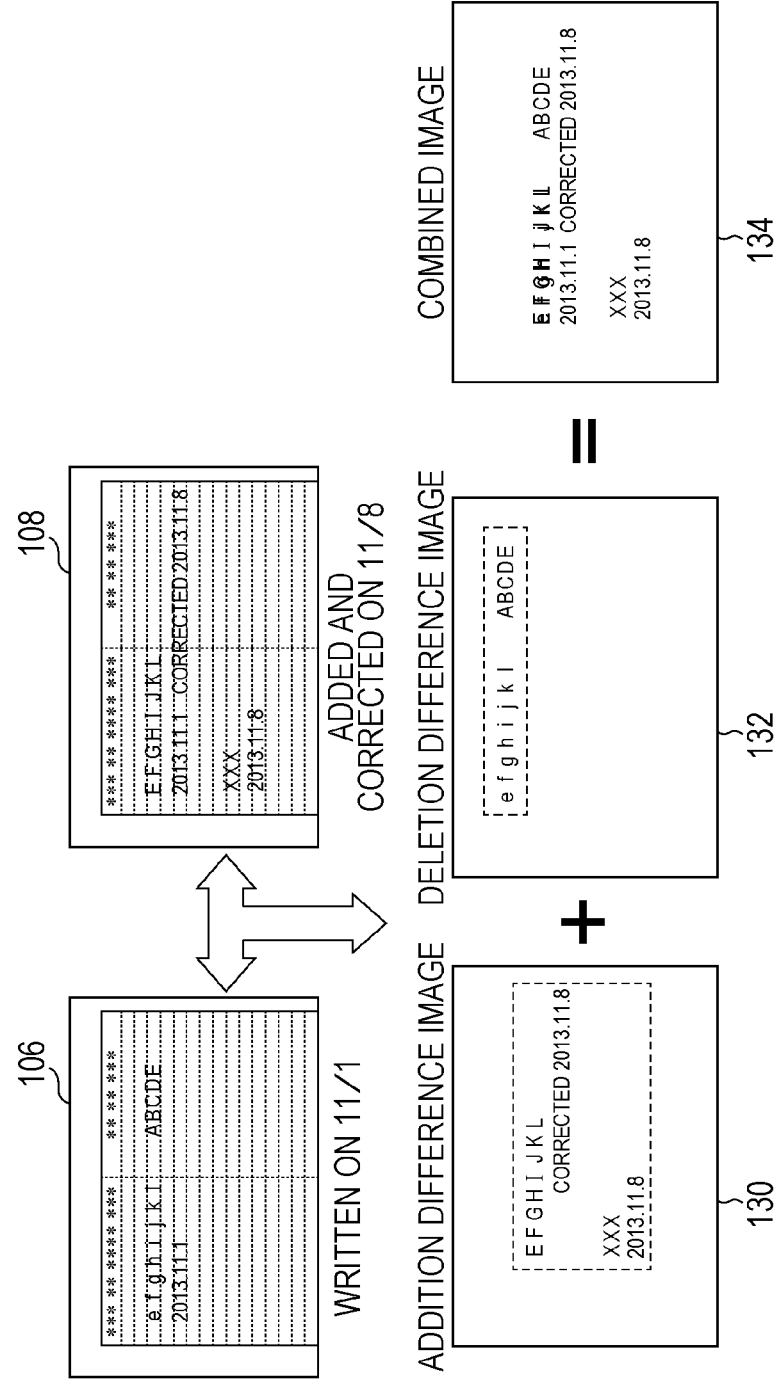
FIG. 5 diagrammatically illustrates a third difference process operation.

An operation in the difference process mode (a third difference process operation) is described below with reference to FIG. 5. In the third difference process operation, writing is performed on the medical record sheet, and written medical record sheet image data 106 is thus generated in November 1. Addition and correction are performed on the medical record sheet in November 8. Part of the written content is rewritten while another part of the written content is deleted. In November 8, the addition is made while the written content is partly deleted. The image on the medical record sheet subsequent to the addition and correction is read by the image reader 12 and medical record sheet image data 108 is thus generated.

The difference image generator 20 extracts a difference between the medical record sheet image data 106 generated in the preceding reading cycle (the preceding image data) and the medical record sheet image data 108 generated in the current reading cycle (the current image data). Addition difference image data 130 representing a portion (addition portion) that is not displayed in the preceding image data but displayed in the current image data is generated. Deletion difference image data 132 representing a portion (deletion portion) that is displayed in the preceding image data but not displayed in the current image data is generated. Attribute information is attached to the addition difference image data 130. The attached attribute information includes difference region location information indicating the location of a difference (addition portion) in the medical record sheet, the addition date and time information indicating the date and time at which the addition is made, the scanning date and time information, and the decoded basic medical information. Attribute information is attached to the deletion difference image data 132. The attached attribute information includes difference region location information indicating the location of a difference (deletion portion) in the medical record sheet, the writing date and time information indicating the date and time at which the deletion is made, the scanning date and time information, and the decoded basic medical information. Combination image data 134 is obtained by combining the addition difference image data 130 and the deletion difference image data 132. In the combination image data 134, the addition portion and the deletion portion are displayed together. By generating the deletion difference image data 132, a correction portion is identified on the medical record sheet. Also, a falsified portion may be possibly identified.

The addition difference image data 130 and the deletion difference image data 132, thus generated, are stored on the image memory 14. The addition difference image data 130 and the deletion difference image data 132 may be transmitted from the image processing apparatus 10 to the server 50, and stored on the image memory 56 in the server 50. The image memory 14 and the server 50 manage each piece of image data in accordance with the attribute information attached thereto.

The third difference process operation generates the addition difference image data 130 representing the portion added to the medical record sheet and the deletion difference image data 132 representing the portion deleted from the medical record sheet. In the same manner as in the first difference process operation, the addition difference image data 130 and the deletion difference image data 132 are generated in the time sequence. With the addition difference image data 130 displayed, the addition portion is displayed. With the deletion difference image data 132 displayed, the deletion portion is displayed.

Figure 6:
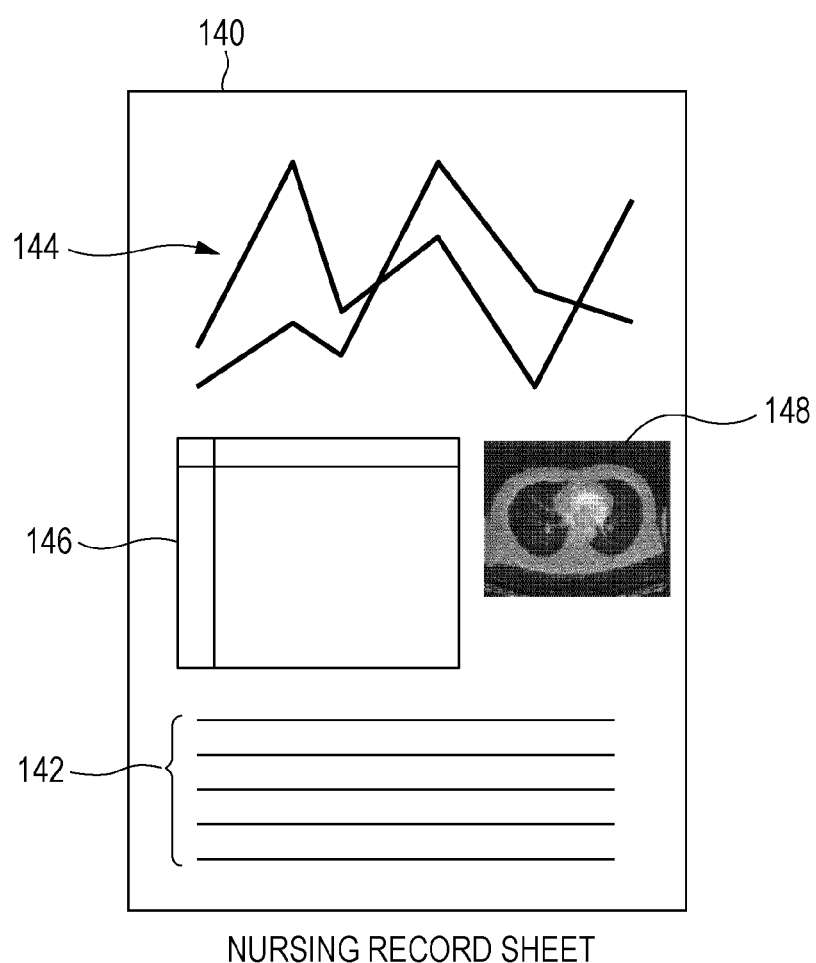
FIG. 6 diagrammatically illustrates an example of a nursing record sheet.

An operation in the difference process mode (a fourth difference process operation) is described with reference to FIG. 6. In the fourth difference process operation, an extraction operation by the region extracting unit 22 is additionally performed. A nursing record sheet is used as an example of the medical record sheet. The same operation as the operation performed on the nursing record sheet is performed on a medical record sheet other than the nursing record sheet (for example, a paper clinical chart or an examination record sheet).

If the image on the nursing record sheet is read by the image reader 12, medical record sheet image data 140 is generated. The nursing record sheet includes a medical record column 142 where a nursing record is written, an examination data column 144 where an examination data, such as a graph, is written or glued, an examination data column 146 where an examination data other than graphs is written or an examination data sheet is glued, and a medical image column 148 where a medical image, such as a photograph, is glued.

The region extracting unit 22 retrieves from the form information memory 24 the sheet form information of the nursing record sheet, and identifies the locations of the medical record column 142, the examination data columns 144 and 146, and the medical image column 148 in the medical record sheet image data 140 in accordance with the sheet form information. The region extracting unit 22 then separates from the medical record sheet image data 140 the region image data of the medical record column 142, the region image data of the examination data column 144, the region image data of the examination data column 146, and the region image data of the medical image column 148. The region extracting unit 22 thus extracts the individual region image data from the medical record sheet image data 140. The attribute information attached to the medical record sheet image data 140 is attached to the region image data. Furthermore, the document type information indicating the corresponding document type and the region location information indicating the location of the region in the nursing record sheet are attached as the attribute information to the region image data. For example, the attribute information attached to the medical record sheet image data 140 is attached to the region image data in the medical record column 142. Furthermore, the document type information indicating the "medical record" and the region location information indicating the location of the "medical record column 142" in the nursing record sheet are attached as the attribute information to the region image data. The attribute information is also attached to the other region image data.

The region image data thus generated is stored on the image memory 14. Also, the region image data may be transmitted from the image processing apparatus 10 to the server 50 and stored on the image memory 56 in the server 50. Each piece of the image data stored in the image memory 14 and the server 50 is managed in accordance with the attribute information attached thereto.

The difference image generator 20 performs a difference process operation responsive to the document type of each region. The difference image generator 20 extracts a difference between the preceding region image data and the current region image data in the medical record column 142. The difference image data representing the difference in the medical record column 142 is thus generated. Difference region location information indicating the location of the difference region in the nursing record sheet and the attribute information attached to the region image data are attached to the difference image data in the medical record column 142. However, the difference image generator 20 does not perform the difference process operation on the examination data columns 144 and 146, and the medical image column 148.

The difference image data in the medical record column 142 is stored on the image memory 14. The difference image data may be transmitted from the image processing apparatus 10 to the server 50 and stored on the image memory 56 in the server 50. The difference image data stored in the image memory 14 and the server 50 is managed in accordance with the attribute information attached thereto.

The medical record column 142 is appropriate as a target of the difference process operation because the addition or the deletion is performed on the written content. In the exemplary embodiment, the difference image data in the medical record column 142 is thus generated. The medical image is not appropriate as a target of the difference process operation because no addition is performed. In the exemplary embodiment, the difference process operation is not performed on the medical image column 148. The examination data is typically represented using a graph or a table, and may not be appropriate as a target of the difference process operation. In the exemplary embodiment, the difference process operation is not performed on the examination data columns 144 and 146. If a graph or a table, as the examination data, is added in the time sequence, however, the difference image generator 20 may perform the difference process operation on the examination data columns 144 and 146.

In the fourth difference process operation, the region image data is generated on a per document type basis. The image of each document type is thus displayed by displaying the region image data. The difference process operation is thus performed on the information suitable as a target for the difference process operation.

FIG. 7 illustrates a management table of the difference image data and the region image data. The management table is stored on the image memory 14 in the image processing apparatus 10. If the difference image data and the region image data are stored on the server 50, the management table is stored on the image memory 56 in the server 50. The management table is created by the image processing apparatus 10 or the server 50 in accordance with the attribute information attached to the difference image data and the region image data. ID in the management table is identification information attached to each piece of the difference image data or the region image data. "Patient ID" identifies each patient. "Document number" is an example of the sheet type information indicating the type of the medical record sheet. For example, number "101" indicates a paper clinical chart, number "102" indicates a nursing record sheet, and number "103" indicates an examination record sheet. "Page number" is a page number of the medical record sheet from which the difference image data or the region image data is extracted. "Region number" indicates each region of the medical record sheet, and is associated with the "document type". For example, region number "1-1" corresponds to "fever chart" (document type 2) in the nursing record sheet, region number "1-2" corresponds to the "examination data" in the nursing record sheet, and region number "1-3" corresponds to the "nursing record" in the nursing record sheet (document type 3). The document type "1" indicates a clinical chart. Coordinates are locations indicated by the difference region location information or the region location information. For example, in the difference image data, the "top left coordinates" and the "bottom right coordinates" of the image respectively represent the "top left coordinates" and the "bottom right coordinates" of the difference region (a rectangular region) of the medical record sheet. In the region image data, if an extracted region is rectangular, the "top left coordinates" and the "bottom right coordinates" of the image respectively represent the "top left coordinates" and the "bottom right coordinates" of the region (rectangular region) of the medical record sheet. Alternatively, the location of the region may be identified by the start point and size of the region. "Recorder" indicates a person who has written the medical record sheet. "Date and time of event" indicates the date and time at which an event, such as diagnosing or writing to the medical record sheet is performed. "Scanning operator" is an example of the operator identification information and indicates an operator who has read the image. "Date and time of scanning" indicates the date and time at which the image reading is performed.

An operation in the display process mode is described below. The difference image data and the region image data may now be stored on the image memory 14 in the image processing apparatus 10. An exemplary embodiment with the difference image data and the region image data stored on the server 50 is described later.

The function of the display processing unit 26 is performed in the display process mode. The display processing unit 26 operates in one of the multiple display modes. The display modes include a reproduction display mode and a layout display mode. In the reproduction display mode, the display processing unit 26 displays the image data on the display 32 in a layout so that the written content of the original medical record sheet is reproduced. In the layout display mode, the display processing unit 26 causes the display 32 to display the image data in accordance with a predetermined layout rule. For example, in the layout display mode, the display processing unit 26 causes the display 32 to display the image data in a time sequence.

In the display process mode, the user enters an image selection condition using the operation unit 34. For example, the image selection condition includes a patient ID, a patient name, an event date and time (a diagnosis date and time or a writing date and time to the medical record sheet), and a scanning date and time. Besides these pieces of information, information included in the attribute information may be input as an image selection condition. When the image selection condition is input, the display processing unit 26 retrieves from the image memory 14 the difference image data and the region image data satisfying the image selection condition based on the image selection condition and the attribute information, and causes the display 32 to display the retrieved image data. If the user specifies a display mode using the operation unit 34, the display processing unit 26 performs a display process operation in response to the display mode specified by the user. The display processing unit 26 may perform a display process operation in accordance with a predetermined display mode.

Examples of the display process operation are described below. The difference image data is displayed in first through fourth display process operations and the difference image data and region image data are displayed in fifth through eight display process operations.

Figure 8:
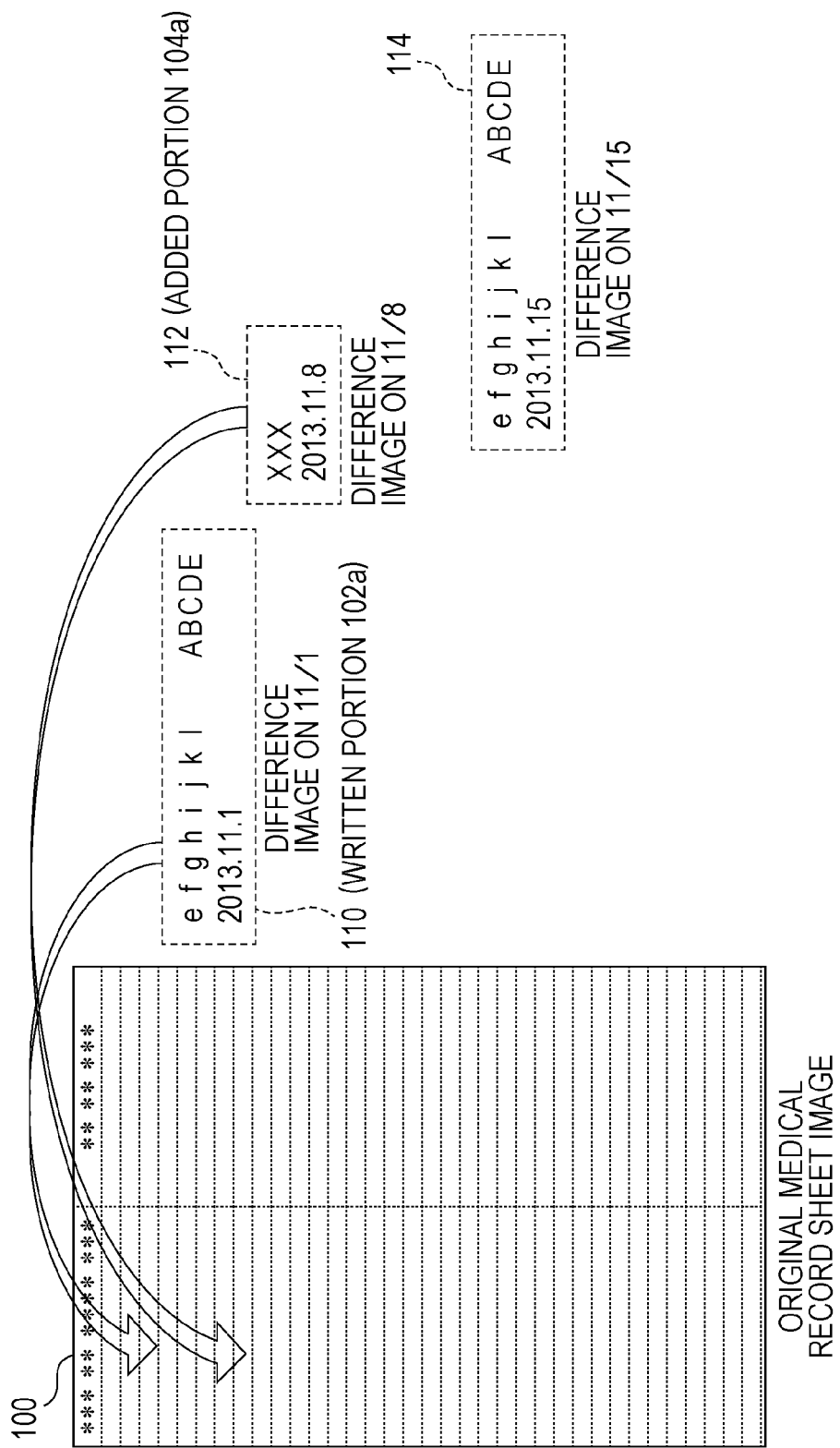
FIG. 8 diagrammatically illustrates a first display process operation.

Referring to FIG. 8, a first display process operation is described. The user may now input the patient ID and the writing date and time to the medical record sheet as an image selection condition. Also, the user may now specify the reproduction display mode as a display mode. In such a case, the display processing unit 26 retrieves from the image memory 14 the difference image data corresponding to the input patient ID and writing date and time. For example, if writing date and time "November 1" and "November 8" are specified as the image selection condition, the display processing unit 26 retrieves from the image memory 14 the difference image data 110 representing the written portion dated November 1 and the difference image data 112 representing the addition portion dated November 8. The display processing unit 26 further retrieves the medical record sheet image data 100 in a blank state from the image memory 14. In accordance with the difference region location information included in the attribute information of the difference image data 110 and 112, the display processing unit 26 overlays the difference image data 110 and 112 on the medical record sheet image data 100 in accordance with the difference region location information respectively included in the attribute information of the difference image data 110 and 112 and causes the display 32 to display the resulting data. More specifically, the display processing unit 26 places the difference image data 110 at a location where the entry portion 102a is written, and the difference image data 112 at a location where the addition portion 104a is added. In the reproduction display mode, the medical record sheet image data 104 of FIG. 3 is constructed in accordance with the medical record sheet image data 100 and the difference image data 110 and 112. If the written date and time "November 15" is specified by the user, the display processing unit 26 overlays difference image data 114 representing an addition portion dated November 15 on the medical record sheet image data 100.

Figure 9:
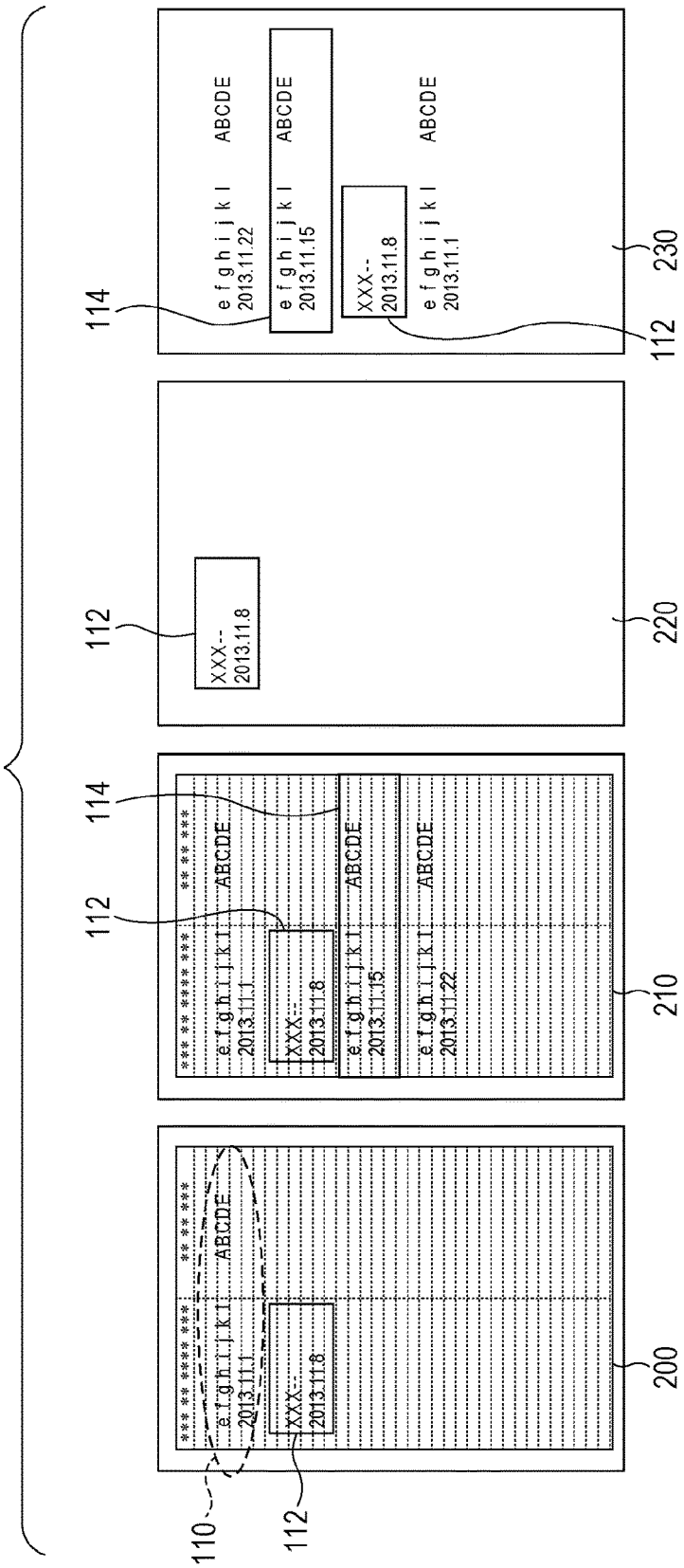
FIG. 9 diagrammatically illustrates the first the display process operation.

Specific difference image data may be emphasized. Such an example is illustrated in FIG. 9. Reproduction image data 200 of FIG. 9 is the blank medical record sheet image data with the difference image data 110 and 112 overlaid thereon in the reproduction display mode. For example, the display processing unit 26 displays latest difference image data 112 in a more emphasized state than the difference image data 110. More specifically, the display processing unit 26 may display the difference image data 110 lighter, may enclose the latest difference image data 112 in a box, or may display the latest difference image data 112 in color. If the user specifies particular date and time (for example, November 8) using the operation unit 34, the display processing unit 26 may display the difference image data 112 representing the addition portion dated November 8 in a more emphasized state than the difference image data 110.

The difference image data of a particular period of time may be emphasized. For example, reproduction image data 210 of FIG. 9 may be the difference image data dated November 1, November 8, November 15, and November 22 overlaid on the blank medical record sheet image data. For example, if the user specifies the emphasis of a target period (from November 8 through November 15) using the operation unit 34, the display processing unit 26 emphasizes the difference image data 112 and 114 falling within the target period.

The difference image data may be displayed without using the medical record sheet image data. For example, as illustrated in image data 220, the display processing unit 26 may display the difference image data 112 corresponding to the writing date and time specified by the user (November 8, for example) in the upper portion of the screen. In such a case, the medical record sheet image data is not displayed.

The difference image data may be displayed in the reverse time sequence. As illustrated in reproduction image data 230, the display processing unit 26 displays the difference image data with younger data placed closer to the top edge of the screen. In this operation, the display processing unit 26 arranges and displays the difference image data using the writing date and time information rather than using the difference region location information attached to the difference image data. For example, if the user specifies a "reverse time sequence display mode" using the operation unit 34, the display processing unit 26 displays the difference image data with younger data placed closer to the top edge of the screen. Since the reproduction image data 210 reflects the state of the original medical record sheet, compared with the reproduction image data 200 the younger addition portions are placed farther from the top to the bottom of the screen. On the other hand, in the reproduction image data 230, the younger addition portions are placed closer to the top of the screen. In such an addition type document as the medical record sheet, addition is typically performed from top to bottom on the sheet. In order to reproduce and view the data in this state, the user simply specifies this display form of the reproduction image data 210 using the operation unit 34. In order to view the latest addition portion with higher priority, the user simply specifies the display form of the reproduction image data 230 using the operation unit 34. The display processing unit 26 displays the difference image data in accordance with the display form specified by the user. Note that the difference image data 112 and 114 are emphasized in the reproduction image data 230.

Figure 10:
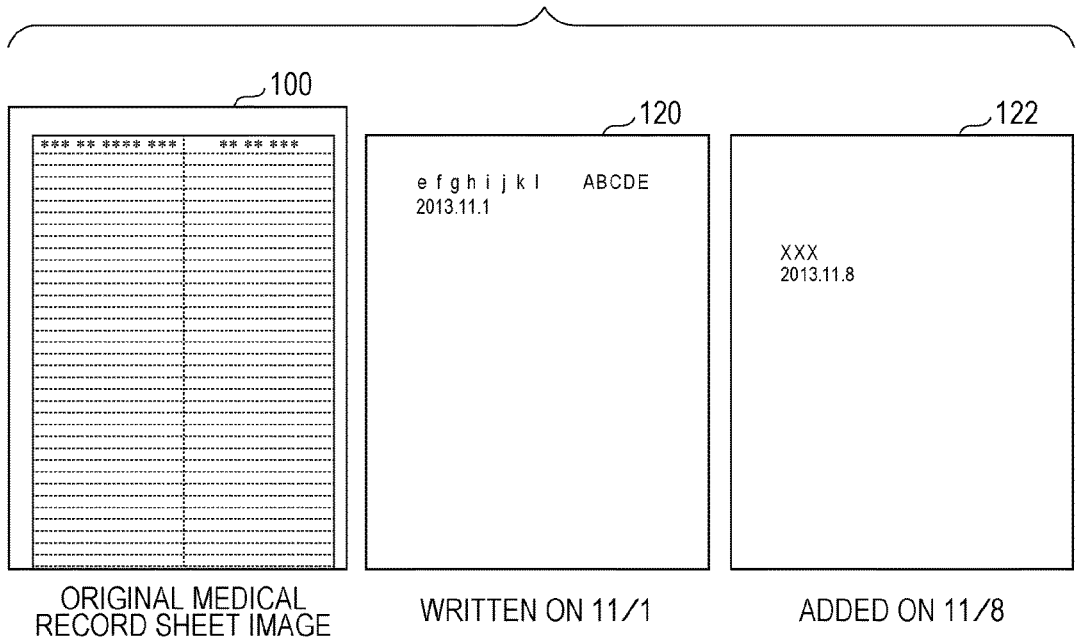
FIG. 10 diagrammatically illustrates a second display process operation.

Referring to FIG. 10, a second display process operation is described. The second display process operation uses the difference image data generated in the second difference process operation. The difference image data 120 and 122 of FIG. 10 is the difference image data generated in the second difference process operation described with reference to FIG. 4, and corresponds to one page of the difference image data with only a portion, corresponding to the difference, displayed. The difference image data 120 dated November 1 and the difference image data 122 dated November 8 may be displayed now. The display processing unit 26 overlays the difference image data 120 and 122 on the blank medical record sheet image data 100. In this operation, the display processing unit 26 overlays the difference image data 120 and 122 on the medical record sheet image data 100 with the background of the difference image data 120 and 122 (regions other than entry portions) set to be transparent. In this way, even if one page of the difference image data is overlaid on another page of the difference image data, the background, the entry portion, and the addition portion of the medical record sheet are displayed without being covered with the background of the difference image data. The second display process operation is free from the difference region location information. Since one page of the difference image data is overlaid on another page of the difference image data, the written content of the original medical record sheet is reproduced without using the difference region location information.

Figure 11:
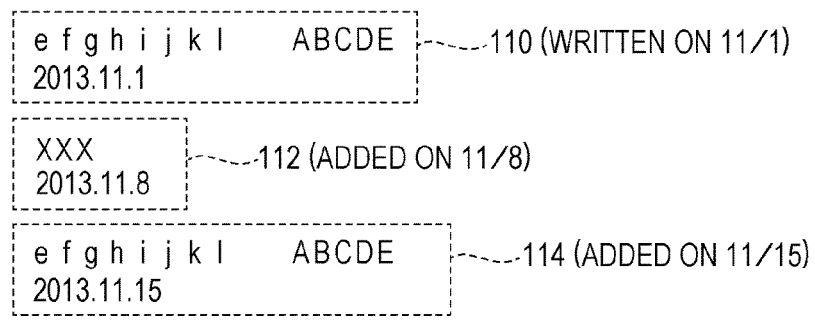
FIG. 11 diagrammatically illustrates a third display process operation.

A third display process operation is described with reference to FIG. 11. FIG. 11 illustrates the third display process operation performed in the layout display mode. The display processing unit 26 displays the difference image data 110, 112, and 114 arranged in the order of writing date and time in the time sequence. The user may specify the layout direction using the operation unit 34. For example, the display processing unit 26 may display the difference image data 110, 112, and 114 arranged in a vertical direction (from top to bottom). The display processing unit 26 may display the difference image data 110, 112, and 114 arranged in a horizontal direction (left to right).

Referring to FIGS. 12A and 12B, a fourth display process operation is described. The fourth display process operation uses the difference image data generated in the third difference process operation. The addition difference image data 130 and the deletion difference image data 132, illustrated in FIG. 12A, are the image data generated in the third difference process operation discussed with reference to FIG. 5. If the addition difference image data 130 and the deletion difference image data 132 are overlaid on each other, the addition portion and the deletion portion are mixed in video as illustrated in combined image data 134. Since the addition portion and the deletion portion are combined in the image data 134, the user may have a problem of being unable to recognize the mixed portion. In the fourth display process operation, the display processing unit 26 may display only the addition difference image data 130 or may display the addition difference image data 130 adjacent to a portion of the deletion difference image data 132 (the addition difference image data 130 below the deletion difference image data 132 in FIG. 12B). In other words, the display processing unit 26 displays the deletion difference image data 132 and the addition difference image data 130 in a juxtaposed position. Since the addition portion and the deletion portion are discriminated in video, the user may easily recognize the addition portion from the deletion portion. Note that the display processing unit 26 may display only deletion difference image data 132.

Referring to FIG. 13, a fifth display process operation is described. In the fifth display process operation, the display processing unit 26 displays the difference image data and the region image data. In the same manner as with the first display process operation, the fifth display process operation is based on the premise that the user has entered the patient ID and the writing date and time as the image selection condition. The display processing unit 26 retrieves from the image memory 14 the difference image data responsive to the entered patient ID and writing date and time. As in the same manner as with the first display process operation, the display processing unit 26 causes the display 32 to display the blank medical record sheet image data with the difference image data overlaid thereon. Reproduction image data 300 of FIG. 13 is the blank medical record sheet image data with the difference image data overlaid thereon, and indicates an entry column of the medical record chart. The display processing unit 26 further retrieves from the image memory 14 region image data 310 and 320 corresponding to the input patient ID. The region image data 310 represents a graph of the nursing record (examination data). The region image data 320 represents examination results (for an examination data sheet). The region image data 310 and 320 is extracted from the medical record sheet image data by the region extracting unit 22. The display processing unit 26 causes the display 32 to display the reproduction image data 300, and the region image data 310 and 320 in a juxtaposed position. In this case, the display processing unit 26 may display the reproduction image data 300 within a reproduction image display window, and the region image data 310 within a region image display window. If the user scrolls the reproduction image data 300 within the display window using the operation unit 34, the display processing unit 26 may scroll the region image data 310 in cooperation with the scrolling operation by the user. For example, the display processing unit 26 associates the top portion of the reproduction image display window with the right-hand portion of the region image display window, and the bottom portion of the reproduction image display window with the left-hand portion of the region image display window. The display processing unit 26 places the difference image data 300 from top to bottom in the time sequence, with the latest image data placed on the bottom portion. In response to the scrolling operation by the user, the display processing unit 26 may scroll the reproduction image data 300 and the region image data 310 in cooperation with each other. The display processing unit 26 may contract or expand the reproduction image data 300 in scale in cooperation with the region image data 310. If the user specifies particular date and time using the operation unit 34, the display processing unit 26 may emphasize, in video, portions in the reproduction image data 300 and the region image data 310 responsive to the date and time specified by the user. In other words, the display processing unit 26 may emphasize, in video, mutually corresponding specified portions (portions of the date and time specified by the user) in the reproduction image data 300 and the region image data 310. For example, if the date "November 15" is specified, the display processing unit 26 display-emphasizes a portion 302 of the difference image data corresponding to that date in the reproduction image data 300. The display processing unit 26 also display-emphasizes a portion 312 corresponding to that date in the region image data 310. For example, if region image data 312 represents a graph, the display processing unit 26 estimates the portion 312 corresponding to the specified date from the scale of the graph, and display-emphasizes the portion 312. If multiple pieces of the region image data 320 are present, the display processing unit 26 may display the multiple pieces of the region image data 320 in an overlaid manner with the region image data 320 of the specified date on top thereof. Multiple pieces of different document types may thus be displayed in cooperation with each other.

A sixth display process operation is described with reference to FIG. 14. In the sixth display process operation, the display processing unit 26 displays a portion of the image data having a relatively lower priority with another piece of image data having a relatively higher priority overlaid thereon. For example, the image data having a relatively higher priority is a portion of the date and time (period) specified by a viewer in the image data. On the other hand, the image data having a relatively lower priority is a remaining portion other than the portion of the date and time specified by the viewer in the image data. As for the priority of the image data, the medical record portion (an entry portion of the clinical chart, an entry portion of the nursing record, a prescription or the like) has the top priority (first priority), the examination results have the second priority, and the graph of the nursing record has the third priority.

The display processing unit 26 causes the display 32 to display the reproduction image data 300 corresponding to the entry portion of the clinical chart, and the region image data 310 corresponding to the graph of the nursing record. If the viewer specifies a particular date using the operation unit 34, the display processing unit 26 display-emphasizes a portion 302 of the difference image data corresponding to the specified date in the reproduction image data 300, and display-emphasizes a portion 312 corresponding to the specified date in the region image data 310. The display processing unit 26 retrieves from the image memory 14 the region image data 320 corresponding to the examination results corresponding to the specified date, and causes the display 32 to display the reproduction image data 300 and the region image data 310 in an overlaid manner. The display processing unit 26 overlays the region image data 320 on other portions than the portions (portions 302 and 312) of the date and time specified by the viewer.

By overlaying the image data having a relatively higher priority on a portion having a relatively lower priority in the image data, the image data useful for the viewer is displayed with a higher priority even in a smaller display area. In a tablet PC displaying the image data, the sixth display process operation is effective.

Figure 15:
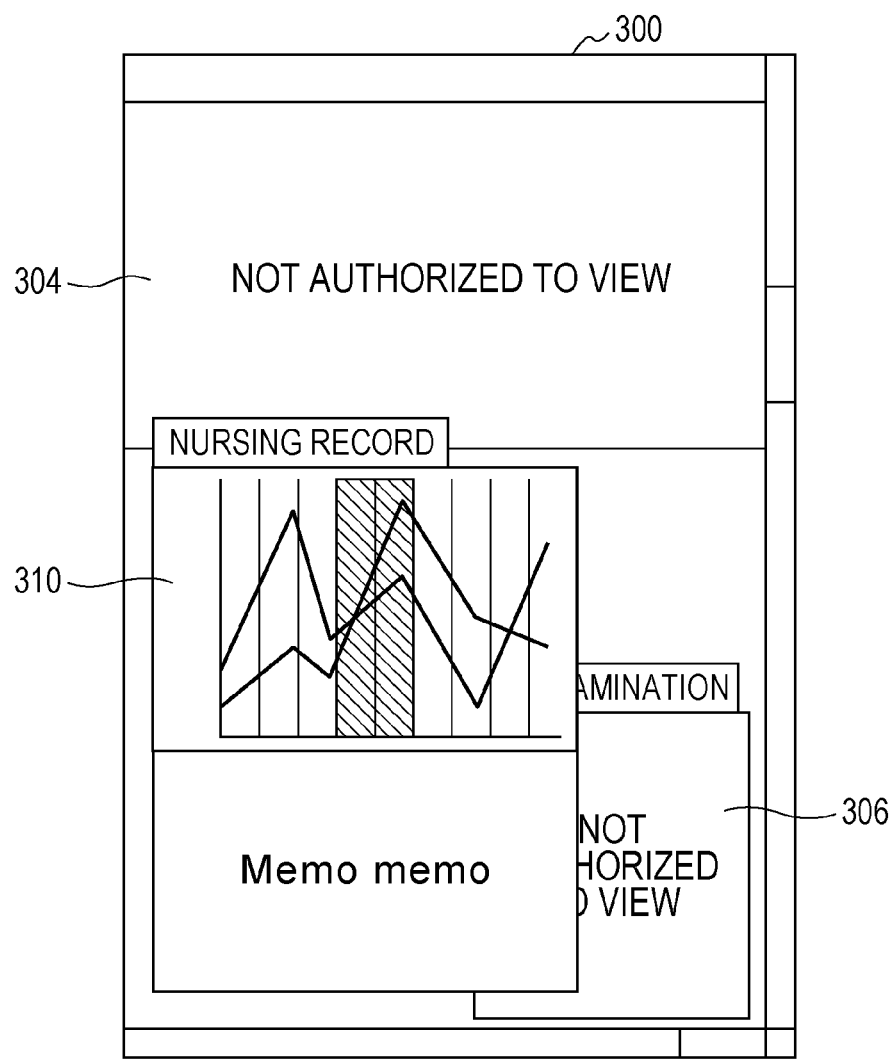
FIG. 15 diagrammatically illustrates a seventh display process operation.

A seventh display process operation is described with reference to FIG. 15. In the seventh display process operation, the displaying of the image data is restricted in response to the viewing right level of the viewer. The image processor 16 or the server 50 attaches, in advance, viewing right level information to the medical record sheet image data, the difference image data, and the region image data. The viewing right level may be set according to the job category (such as doctor, nurse, technician, care worker, and the like). In the display process mode, the viewer enters the viewing right level information using the operation unit 34. In accordance with the viewing right level information, the display processing unit 26 selects image data that is permitted to view out of the image data satisfying the image selection condition, and causes the display 32 to display the selected image data. As illustrated in FIG. 15, for example, if the user is not authorized to view the written content of the clinical chart, the display processing unit 26 displays a substitute image 304 in place of that portion of the clinical chart. Similarly, if the viewer is not authorized to view the examination results, the display processing unit 26 displays a substitute image 306.

The display processing unit 26 may restrict the displaying of the image data depending on whether the viewer is in charge of the patient or not. For example, the attribute information may include ID (such as a doctor ID or a nurse ID) indicating a person in charge (a doctor in charge or a nurse in charge), and attaches the attribute information to the medical record sheet image data, the difference image data, and the region image data. The display processing unit 26 then determines whether the viewer is in charge of the patient based on the ID input by the viewer using the operation unit 34 and the ID included in the attribute information of the image data satisfying the image selection condition. If the viewer is in charge of the patient, the display processing unit 26 causes the display 32 to display the image data satisfying the image selection condition. If the viewer is not in charge of the patient, the display processing unit 26 restricts the displaying of the image data. A person-in-charge management table that associates the patient ID of a patient with a person in charge of the patient (such as a doctor or a nurse in charge of the patient) is prepared, and the display processing unit 26 may determine whether the viewer is in charge of the patient, based on the person-in-charge management table.

In the seventh display process operation, the displaying of the image data is restricted according to the job category of the viewer. The displaying of the image data that may be probably unnecessary in a job practice is thus restricted. This arrangement controls the leaking of private information. Similarly, the displaying of the image data related to a patient the viewer is not in charge of is restricted. The displaying of the image data that may be unnecessary in a job practice is restricted.

Figure 16:
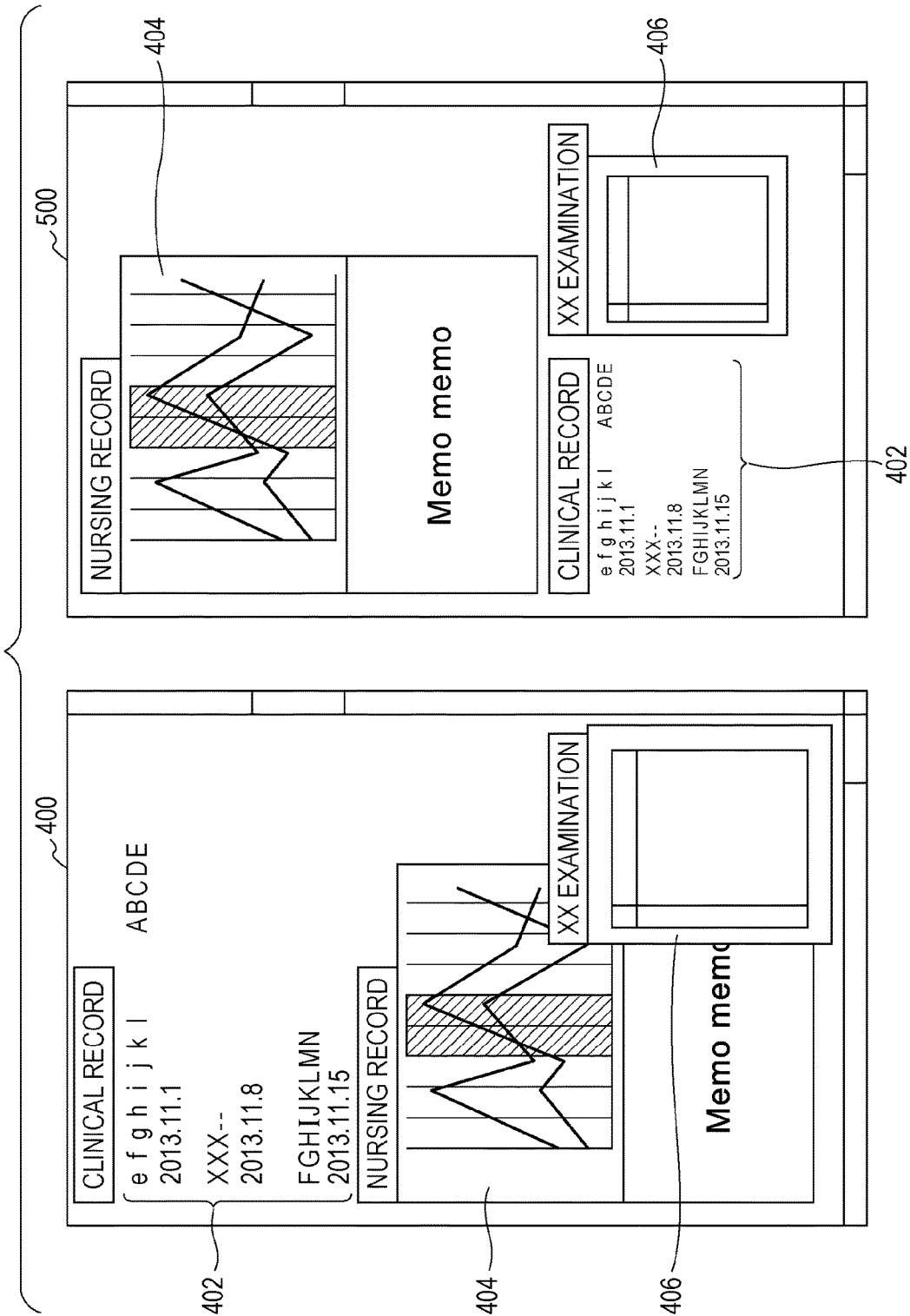
FIG. 16 diagrammatically illustrates an eighth display process operation.

An eighth display process operation is described with reference to FIG. 16. In the eight display process operation, the display processing unit 26 changes the display form of the image data in response to the job category of the viewer (viewing right level). For example, if the viewer is a doctor, the medical record such as the clinical chart has the top priority (first priority), the examination results have the second priority, and the nursing record has the third priority. If the viewer is a nurse, the nursing record has the top priority (first priority), and the medical record and the examination results have the second priority. The image processor 16 or the server 50 attaches priority information indicating a priority level of each job category of each viewer (viewing right level information) to the medical record sheet image data, the difference image data, and the region image data. In the display mode, the viewer enters the viewing right level information using the operation unit 34. The display processing unit 26 displays the image data in a display form responsive to the priority level corresponding to the viewing right level information.

If the viewer is a doctor, the display processing unit 26 causes the display 32 to display image data 400 for doctors. The display processing unit 26 expands reproduction image data 402 representing a medical record, such as a clinical chart (information having the first priority), and displays the reproduction image data 402 in the upper portion of the image data 400. The display processing unit 26 expands and displays region image data 406 representing the examination results (information having the second priority). If display space is not large enough, the display processing unit 26 displays the region image data 406 having the second priority overlaid on region image data 404 indicating the nursing record (having the third priority).

On the other hand, if the viewer is a nurse, the display processing unit 26 causes the display 32 to display image data 500 for nurses. The display processing unit 26 expands the region image data 404 representing the nursing record (information having the first priority) and displays the region image data 404 in the upper portion of the image data 500. The display processing unit 26 contracts the reproduction image data 402 representing the medical record and the region image data 406 representing the examination results, and then displays the reproduction image data 402 and the region image data 406 in the lower portion of the image data 500.

In the eighth display process operation, the image data is displayed in the display form responsive to the job category of the viewer. The operational efficiency of the viewer may thus be increased.

In the exemplary embodiment, the difference image data arranged in the time sequence and the region image data arranged on a per document type basis are generated. The image data is thus displayed in the display form satisfying the request of each viewer without greatly changing the manner of an operation based on paper documents.

Figure 17:
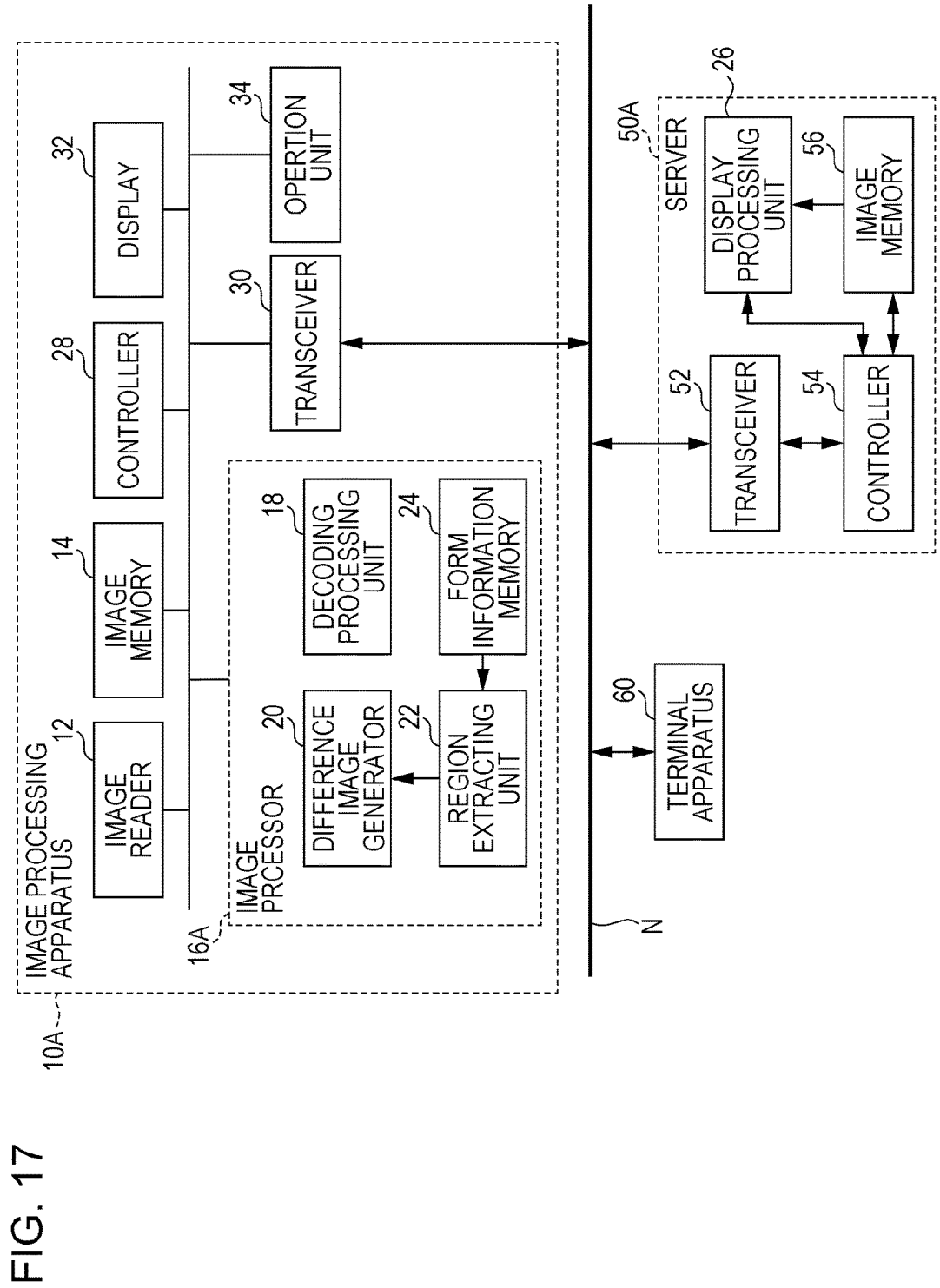
FIG. 17 is a block diagram illustrating an example of a system as a modification of the exemplary embodiment.

FIG. 17 illustrates a system of a modification of the exemplary embodiment. The system as the modification of the exemplary embodiment includes an image processing apparatus 10A and a server 50A. In the modification, the image processing apparatus 10A performs the difference process operation and region extraction process operation while the server 50A performs the display process operation. More specifically, the display processing unit 26 is not included in the image processing apparatus 10A but included in the server 50A. The medical record sheet image data, the difference image data, and the region image data are generated by an image processor 16A and transmitted to the server 50A to be stored on the image memory 56 in the server 50A. In response to a request from the terminal apparatus 60, the server 50A transmits the image data responsive to the request to the terminal apparatus 60. In this way, the terminal apparatus 60 displays the image data.

The display processing unit 26 executes the same process operations as those of the above exemplary embodiment (the first through eighth display process operations). The image data generated in one of the first through eighth display process operations is transmitted from the server 50A to the terminal apparatus 60 to be displayed there.

The viewer accesses the server 50A using the terminal apparatus 60. Using the terminal apparatus 60, the viewer enters the image selection condition, such as the patient ID of a patient as a viewing target and writing date (addition date), and specifies the display mode. The information indicating the image selection condition and the display mode is transmitted from the terminal apparatus 60 to the server 50A. The display processing unit 26 in the server 50A generates the display image data in accordance with the image selection condition and the display mode. The display image data is transmitted from the server 50A to the terminal apparatus 60 to be displayed there.

In the first display process operation of FIG. 9, the server 50A generates the reproduction image data 200, the reproduction image data 210, the image data 220, or the reproduction image data 230. These pieces of image data are transmitted from the server 50A to the terminal apparatus 60 to be displayed there.

In the second display process operation of FIG. 10, the server 50A generates the display image data with the difference image data 120 and 122 overlaid on the blank medical record sheet image data 100. The display image data is transmitted from the server 50A to the terminal apparatus 60 to be displayed there.

In the third display process operation of FIG. 11, the difference image data 110, 112, and 114 is transmitted from the server 50A to the terminal apparatus 60. The terminal apparatus 60 displays the difference image data 110, 112, and 114 in the time sequence.

In the fourth display process operation of FIGS. 12A and 12B, the addition difference image data 130 and the deletion difference image data 132 are transmitted from the server 50A to the terminal apparatus 60. The terminal apparatus 60 displays the addition difference image data 130 and the deletion difference image data 132 in a juxtaposed position as illustrated in FIG. 12B.

Figure 14:
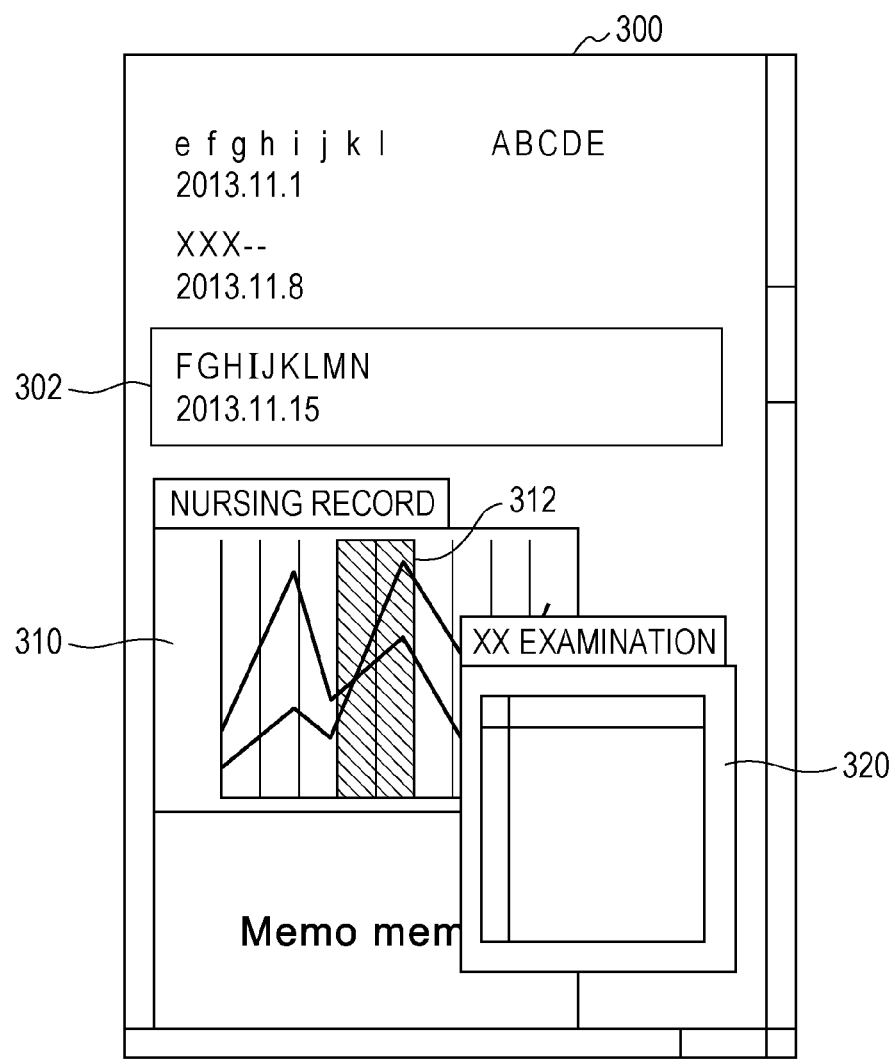
FIG. 14 diagrammatically illustrates a sixth display process operation.

In the fifth and sixth display process operations of FIG. 13 and FIG. 14, the reproduction image data 300, and the region image data 310 and 320 are transmitted from the server 50A to the terminal apparatus 60. The terminal apparatus 60 displays the reproduction image data 300, and the region image data 310 and 320. As illustrated in FIG. 13, the terminal apparatus 60 displays the reproduction image data 300, and the region image data 310 and 320 in a juxtaposed position, and the portion of the date specified by the viewer is display-emphasized. As illustrated in FIG. 14, the terminal apparatus 60 displays the reproduction image data 300, and the region image data 310 and 320 in a overlaid manner. The display process operation is then performed with the priority considered in the same manner as in the six display process operation. If the terminal apparatus 60 is a tablet PC having a limited display area, the sixth display process operation is particularly effective.

In the seventh display process operation of FIG. 15, the terminal apparatus 60 displays the image data the viewer is authorized to view. In the eighth display process operation of FIG. 16, the terminal apparatus 60 displays the image data in the display form matching the job category of the viewer.

Since the medical record sheet image data, the difference image data, and the region image data are stored on the server 50A as described above, the image data is shared. The terminal apparatus 60 thus displays the image data in the display form satisfying the request of each viewer without greatly changing the manner of an operation based on paper documents.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An image processing apparatus comprising:
   at least one hardware processor configured to implement:
   a difference image generator that receives a collection of medical record sheet image data that is generated by reading an image of a medical record sheet with content thereof updated in a time sequence, extracts a difference between the medical record sheet image data that is generated in a preceding image reading cycle and the medical record sheet image data that is generated in a subsequent image reading cycle, and acquires a sequential collection of difference image data representing an updated written portion of the medical record sheet by extracting a difference in each image reading cycle;
   a memory processing unit that associates the difference image data with attribute information related to writing, and causes a memory to store the difference image data with the attribute information associated therewith;

an output processing unit that selects output image data from the collection of difference image data in accordance with a specified image selection condition and the attribute information and outputs the selected output image data; and a region extracting unit that identifies a document type of each region in the medical record sheet and extracts region image data representing each region from the medical record sheet image data, wherein the difference image generator extracts a difference between one region and another region of each document type.

2. The image processing apparatus according to claim 1, wherein the attribute information comprises chronological information related to date and time at which the medical record sheet is updated, and wherein the image selection condition comprises a condition related to the date and time.

3. The image processing apparatus according to claim 1, wherein the output processing unit operates in a reproduction display mode to display the output image data in a state where the written content of the medical record sheet is reproduced or in a layout display mode to display the output image data in a state where the output image data is arranged in the time sequence.

4. The image processing apparatus according to claim 2, wherein the output processing unit operates in a reproduction display mode to display the output image data in a state where the written content of the medical record sheet is reproduced or in a layout display mode to display the output image data in a state where the output image data is arranged in the time sequence.

5. The image processing apparatus according to claim 3, wherein the attribute information comprises difference region location information indicating a location of a difference region in the medical record sheet, and wherein the output processing unit displays, in the reproduction display mode, the output image data in the state that reflects the written content of the medical record sheet based on the difference region location information.

6. The image processing apparatus according to claim 4, wherein the attribute information comprises difference region location information indicating a location of a difference region in the medical record sheet, and wherein the output processing unit displays, in the reproduction display mode, the output image data in the state that reflects the written content of the medical record sheet based on the difference region location information.

7. The image processing apparatus according to claim 1, wherein the medical record sheet is a sheet which content is added to or deleted from in the time sequence, and wherein the difference image generator generates, as the difference image data, at least, addition difference image data representing a newly added portion to the medical record sheet or deletion difference image data representing a newly deleted portion from the medical record sheet.

8. The image processing apparatus according to claim 2, wherein the medical record sheet is a sheet which content is added to or deleted from in the time sequence, and wherein the difference image generator generates, as the difference image data, at least, addition difference image data representing a newly added portion to the medical record sheet or deletion difference image data representing a newly deleted portion from the medical record sheet.

9. The image processing apparatus according to claim 2, further comprising a region extracting unit that identifies a document type of each region in the medical record sheet and extracts region image data representing each region from the medical record sheet image data, wherein the difference image generator extracts a difference between one region and another region of each document type.

10. The image processing apparatus according to claim 1, wherein the medical record sheet comprises, as the document type, a medical record section where a medical record is written, an examination data section where examination data is written or an examination data sheet is attached, and a medical image section where a medical image is glued, and wherein the difference image generator generates the collection of difference image data of the medical record section out of the medical record section, the examination data section, and the medical image section.

11. The image processing apparatus according to claim 10, wherein the memory processing unit associates the region image data with document type information indicative of the document type as attribute information and causes the memory to store the region image data with the attribute information associated therewith, wherein the image selection condition comprises a condition related to the document type, and wherein the output processing unit selects the output image data from the collection of difference image data in accordance with the image selection condition and the attribute information and outputs the output image data, and outputs the region image data as the output image data.

12. The image processing apparatus according to claim 11, wherein the output processing unit displays a plurality of pieces of output image data different in document type with specified sections thereof corresponding to each other thereacross discriminated from other sections.

13. The image processing apparatus according to claim 11, wherein the output processing unit displays a plurality of pieces of output image data of same document type in an overlaid manner.

14. The image processing apparatus according to claim 11, wherein the output processing unit displays a plurality of pieces of output image data different in document type in a manner such that if one piece of the output image data is scrolled in response to an operation of a viewer, the other pieces of the output image data are scrolled in cooperation therewith.

15. The image processing apparatus according to claim 11, wherein the output processing unit displays a plurality of pieces of output image data in a manner such that one piece of the output image data having a relatively higher priority overlays another piece of the output image data having a relatively lower priority.

16. The image processing apparatus according to claim 11, wherein the output processing unit restricts the output of the output image data in accordance with a viewing right level of a viewer.

17. The image processing apparatus according to claim 11, wherein the output processing unit changes a display form of the output image data in accordance with a job category of a viewer.

18. An image processing method implemented by at least one hardware processor, the image processing method comprising:

receiving a collection of medical record sheet image data that is generated by reading an image of a medical record sheet with content thereof updated in a time sequence, extracting a difference between the medical record sheet image data that is generated in a preceding image reading cycle and the medical record sheet image data that is generated in a subsequent image reading cycle, and acquiring a sequential collection of difference image data representing an updated written portion of the medical record sheet by extracting a difference in each image reading cycle;

associating the difference image data with attribute information related to writing, and causing a memory to store the difference image data with the attribute information associated therewith;

selecting output image data from the collection of difference image data in accordance with a specified image selection condition and the attribute information, and outputting the selected output image data;

identifying a document type of each region in the medical record sheet;

extracting region image data representing each region from the medical record sheet image data; and extracting a difference between one region and another region of each document type.

19. A non-transitory computer readable medium storing a program causing a computer to execute a process for processing an image, the process comprising:

receiving a collection of medical record sheet image data that is generated by reading an image of a medical record sheet with content thereof updated in a time sequence, extracting a difference between the medical record sheet image data that is generated in a preceding image reading cycle and the medical record sheet image data that is generated in a subsequent image reading cycle, and acquiring a sequential collection of difference image data representing an updated written portion of the medical record sheet by extracting a difference in each image reading cycle;

associating the difference image data with attribute information related to writing, and causing a memory to store the difference image data with the attribute information associated therewith;

selecting output image data from the collection of difference image data in accordance with a specified image selection condition and the attribute information, and outputting the selected output image data;

identifying a document type of each region in the medical record sheet;

extracting region image data representing each region from the medical record sheet image data; and extracting a difference between one region and another region of each document type.

20. An image processing apparatus comprising:

at least one hardware processor configured to implement:

an inputting unit that inputs a first document at a first timing and a second document at a second timing, the second document being a document which comprises the first document and a modification made to the first document;

a difference image generator that extracts a difference between the first document and the second document;

a memory that stores information indicating the extracted difference, the second timing and a third timing, when the modification is made to the first document, in association with each other;

a reception unit that receives a condition regarding a timing from a user; and an outputting unit that, in response to the received timing matching the third timing, outputs an image which comprises the first document and the difference image.

* * * * *